United States Patent
Bachinski et al.

(10) Patent No.: US 8,977,366 B2
(45) Date of Patent: Mar. 10, 2015

(54) SYSTEMS AND METHODS FOR THERAPEUTIC ELECTRICAL STIMULATION

(71) Applicant: EMPI Inc., Vista, CA (US)

(72) Inventors: Thomas Jerome Bachinski, Lakeville, MN (US); Richard Paul Shindley, Big Lake, MN (US); Dennis Lutz, Lino Lakes, MN (US)

(73) Assignee: EMPI Inc., Vista, CA (US)

( * ) Notice: Subject to any disclaimer, the term of this patent is extended or adjusted under 35 U.S.C. 154(b) by 0 days.

(21) Appl. No.: 14/322,838

(22) Filed: Jul. 2, 2014

(65) Prior Publication Data

US 2014/0316507 A1     Oct. 23, 2014

Related U.S. Application Data

(60) Continuation of application No. 13/743,569, filed on Jan. 17, 2013, now Pat. No. 8,798,739, which is a division of application No. 12/276,068, filed on Nov. 21, 2008, now Pat. No. 8,386,032.

(60) Provisional application No. 61/019,489, filed on Jan. 7, 2008.

(51) Int. Cl.
*A61N 1/00* (2006.01)
*A61N 1/04* (2006.01)

(52) U.S. Cl.
CPC .............. *A61N 1/048* (2013.01); *A61N 1/0492* (2013.01)
USPC .................. 607/115; 607/2; 607/46; 607/117

(58) Field of Classification Search
USPC ........................ 607/2, 46, 115, 117
See application file for complete search history.

(56) References Cited

U.S. PATENT DOCUMENTS

| | | | |
|---|---|---|---|
| 1,428,358 A | 9/1922 | Burbery | |
| 3,895,635 A | 7/1975 | Justus et al. | |

(Continued)

FOREIGN PATENT DOCUMENTS

| | | | |
|---|---|---|---|
| FR | 964611 A | 5/1950 | |
| GB | 257145 A | 8/1926 | |

(Continued)

OTHER PUBLICATIONS

Extended European Search Report dated Dec. 14, 2010 in European Patent Application No. 09700152.3-2305 12237831.

(Continued)

*Primary Examiner* — Nicole F Lavert
(74) *Attorney, Agent, or Firm* — Knobbe Martens Olson & Bear LLP

(57) ABSTRACT

A patch for a therapeutic electrical stimulation device includes a shoe connected to the first side of the patch, the shoe including a body extending in a longitudinal direction from a first end to a second end, and having first and second surfaces, the first end of the shoe defining at least two ports, and the first surface of the shoe defining a connection member. The patch also includes at least one conductor positioned in the ports of the first end of the shoe. The shoe is configured for sliding insertion into a receptacle defined by a controller so that the conductor is connected to the controller to deliver electrical current from the controller, through the conductor, and to the electrodes, and the connection member is at least partially captured by a detent defined by the controller in the receptacle to retain the shoe within the receptacle.

6 Claims, 30 Drawing Sheets

(56) References Cited

U.S. PATENT DOCUMENTS

| | | |
|---|---|---|
| 4,040,697 A | 8/1977 | Ramsay et al. |
| 4,178,052 A | 12/1979 | Ekbom et al. |
| 4,253,721 A | 3/1981 | Kaufman |
| 4,268,101 A | 5/1981 | Stone |
| 4,390,223 A | 6/1983 | Zenkich |
| 4,671,591 A | 6/1987 | Archer |
| 4,690,144 A | 9/1987 | Rise et al. |
| 5,277,613 A | 1/1994 | Neward |
| 5,326,272 A | 7/1994 | Harhen et al. |
| 5,466,017 A | 11/1995 | Szabo et al. |
| 5,498,235 A | 3/1996 | Flower |
| 5,562,607 A | 10/1996 | Gyory |
| 5,562,707 A | 10/1996 | Prochazka et al. |
| 5,895,298 A | 4/1999 | Faupel et al. |
| 5,895,369 A | 4/1999 | Flower |
| 6,445,955 B1 | 9/2002 | Michelson et al. |
| 6,687,536 B1 | 2/2004 | Beck et al. |
| 7,066,767 B2 | 6/2006 | Liao |
| 7,214,107 B2 | 5/2007 | Powell et al. |
| 7,255,609 B1 | 8/2007 | Epstein |
| 7,270,580 B2 | 9/2007 | Bradley et al. |
| 7,364,440 B2 | 4/2008 | Gobron et al. |
| 7,574,262 B2 | 8/2009 | Haugland et al. |
| 2004/0039275 A1 | 2/2004 | Sato et al. |
| 2004/0072475 A1 | 4/2004 | Istvan |
| 2004/0106964 A1 | 6/2004 | Fischer et al. |
| 2005/0107841 A1 | 5/2005 | Meadows et al. |
| 2005/0131506 A1 | 6/2005 | Rezai et al. |
| 2005/0181341 A1 | 8/2005 | Ewing et al. |
| 2006/0195152 A1 | 8/2006 | Gerber |
| 2007/0088419 A1 | 4/2007 | Fiorina et al. |
| 2007/0191912 A1 | 8/2007 | Fischer et al. |
| 2008/0254684 A1 | 10/2008 | Tracy et al. |
| 2009/0149731 A1 | 6/2009 | Selvitelli et al. |
| 2009/0182393 A1 | 7/2009 | Bachinski et al. |
| 2009/0182394 A1 | 7/2009 | Bachinski |

FOREIGN PATENT DOCUMENTS

| | | |
|---|---|---|
| WO | WO-01/03768 A1 | 1/2001 |
| WO | WO-2006/113801 A2 | 10/2006 |
| WO | WO-2009/148595 A2 | 12/2009 |

OTHER PUBLICATIONS

International Search Report and Written Opinion dated Dec. 20, 2011 in International Application No. PCT/US2011/047398.

International Search Report and Written Opinion in International Application No. PCT/US2006/012270.

Notice of Allowance in U.S. Appl. No. 12/856,382 dated Feb. 16, 2012.

Notice of Allowance in U.S. Appl. No. 12/276,068 dated Oct. 17, 2012.

Notice of Allowance in U.S. Appl. No. 12/319,539 dated Jan. 29, 2013.

| Figure 19-1 |
| Figure 19-2 |

| Figure 20 | Figure 20-3 |
| --- | --- |
| | Figure 20-2 |
| | Figure 20-1 |

| Figure 21 | Figure 21-3 |
| --- | --- |
| | Figure 21-2 |
| | Figure 21-1 |

SYSTEMS AND METHODS FOR THERAPEUTIC ELECTRICAL STIMULATION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/743,569, filed on Jan. 17, 2013, which is a division of U.S. application Ser. No. 12/276,068, filed Nov. 21, 2008, now U.S. Pat. No. 8,386,032, which claims the benefit of U.S. Patent Application Ser. No. 61/019,489 filed on Jan. 7, 2008. Each of the aforementioned applications is incorporated by reference herein in its entirety, and each is hereby expressly made a part of this specification.

BACKGROUND

Low-power electrical stimulation has been found to have various therapeutic uses. One example of low-power electrical stimulation is transcutaneous electrical nerve stimulation ("TENS"). TENS devices typically operate by generating low-power electrical impulses that are supplied to the skin of a patient through electrodes. The electrical impulses have been found to diminish or completely relieve pain previously felt by a patient.

There are two primary theories for the effectiveness of TENS devices. The first theory is the Gate Control Theory. In this theory, the mild electrical stimulation is thought to relieve pain in a similar way as when an injured area is manually rubbed. Rubbing acts to mask the pain from the injury. Similarly, when electrical impulses pass through the skin they pass through portions of the peripheral nervous system. The electrical impulses reduce the transmission of pain messages, thereby diminishing or completely relieving pain.

A second theory is the Endorphin Release Theory. This theory states that the electrical impulses from the TENS device cause mild to moderate muscle twitching in the body. The body responds to the muscle twitching by producing natural pain relievers called endorphins, thereby diminishing or completely relieving the pain.

In addition to TENS, electrical stimulation has also been found to be useful for other therapies. Examples include edema reduction, wound healing, iontophoresis drug delivery, muscle stimulation, and interferential current therapy.

SUMMARY

In general terms, this disclosure is directed to therapeutic electrical stimulation. One aspect is a therapeutic electrical stimulation device comprising a controller, the controller including a power source, an electrical signal generator, and a receptacle, wherein the electrical signal generator is electrically coupled to the power source, and wherein the electrical signal generator generates electrical signals that are provided to a conductor associated with the receptacle; and a patch arranged to convey the electrical signals from the controller, the patch including a shoe, an insulating layer, and electrodes, wherein the shoe is removably connected to the controller at the receptacle, wherein the shoe is electrically coupled to the conductor, and wherein the electrodes are electrically coupled to the shoe.

Another aspect is a controller for a therapeutic electrical stimulation device, the controller comprising a power source including a rechargeable battery; an electrical signal generator powered by the power source and generating an electrical signal, and a receptacle including at least one conductor, the conductor electrically coupled to the electrical signal generator to receive the electrical signal, the receptacle arranged and configured to receive a portion of a patch to electrically couple a portion of the patch with the conductor.

Yet another aspect is a patch for a therapeutic electrical stimulation device, the patch comprising an insulating layer having a first side and a second side; a shoe connected to the first side of the patch and including at least two conductors, wherein the shoe is configured for insertion into a receptacle of a controller of the therapeutic electrical stimulation device; at least two electrodes adjacent the second side of the patch, wherein each conductor is electrically coupled to one of the electrodes; and an adhesive layer connected to the second side of the insulating layer.

A further aspect is a method of connecting a patch with a controller of a therapeutic electrical stimulation device, the method comprising advancing the controller in a first direction toward that patch to insert a shoe of the patch into a receptacle of the controller; and advancing the controller in a second direction to cause the controller to engage with the shoe.

Another aspect is a method of adjusting the operation of a therapeutic electrical stimulation device, the method comprising operating the therapeutic electrical stimulation device in a first mode by executing a first firmware algorithm; downloading a second firmware algorithm; installing the second firmware algorithm onto the therapeutic electrical stimulation device; and executing the second firmware algorithm to operate the therapeutic electrical stimulation device in a second mode.

A further aspect is a docking station comprising a housing; a slot in the housing arranged and configured to receive a therapeutic electrical stimulation device; a power source for supplying power to a therapeutic electrical stimulation device to recharge a battery; and a data communication device for communicating between the therapeutic electrical stimulation device and a communication network.

This summary is provided to introduce a selection of concepts in a simplified form that are further described below in the Detailed Description. This Summary is not intended to identify key or essential features of the claimed subject matter, nor is it intended to be used in any way as to limit the scope of the claimed subject matter.

DETAILED DESCRIPTION

Figure 1:
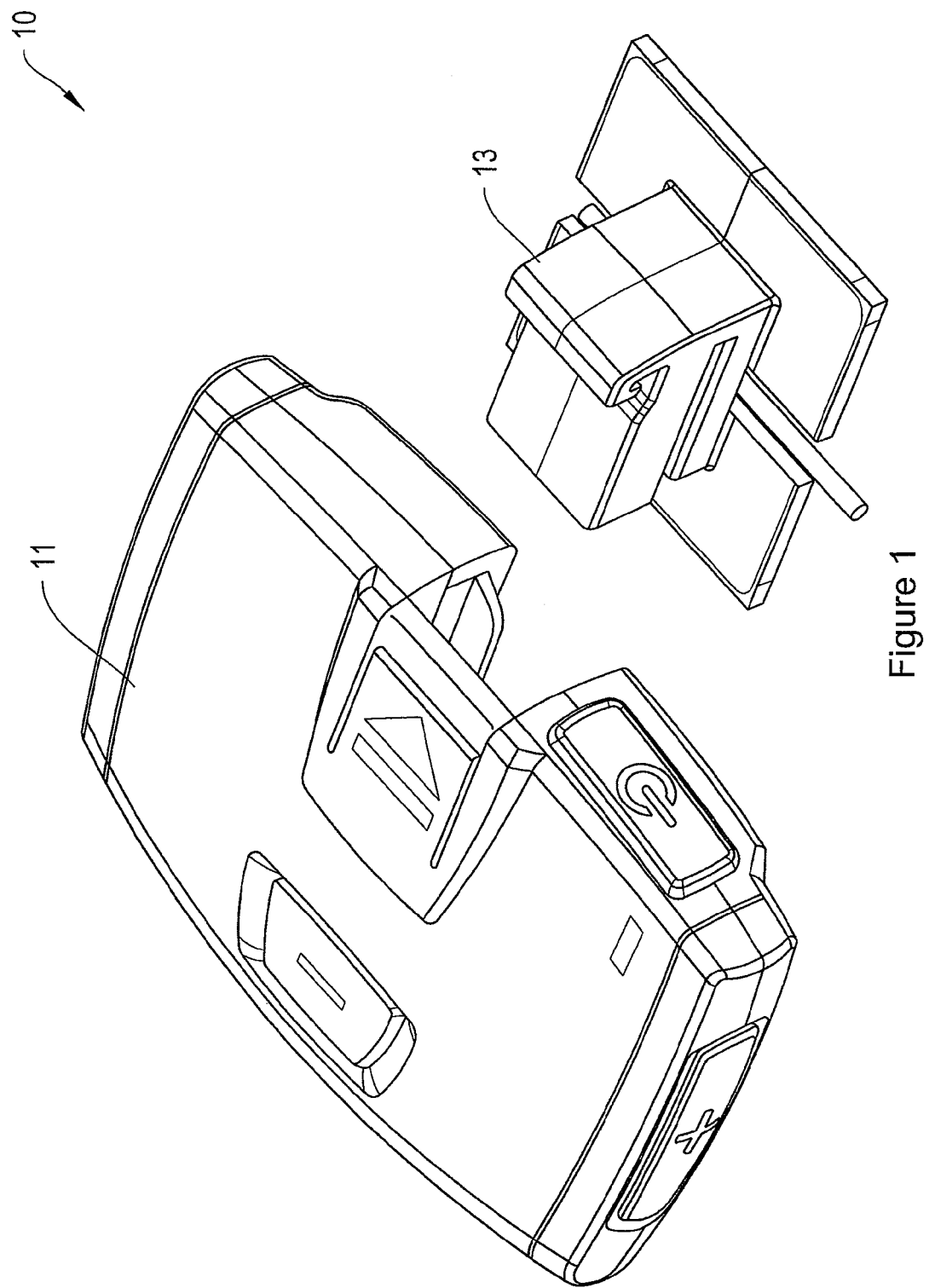
FIG. 1 is a perspective top view of an example therapeutic electrical stimulation device.
Figure 2:
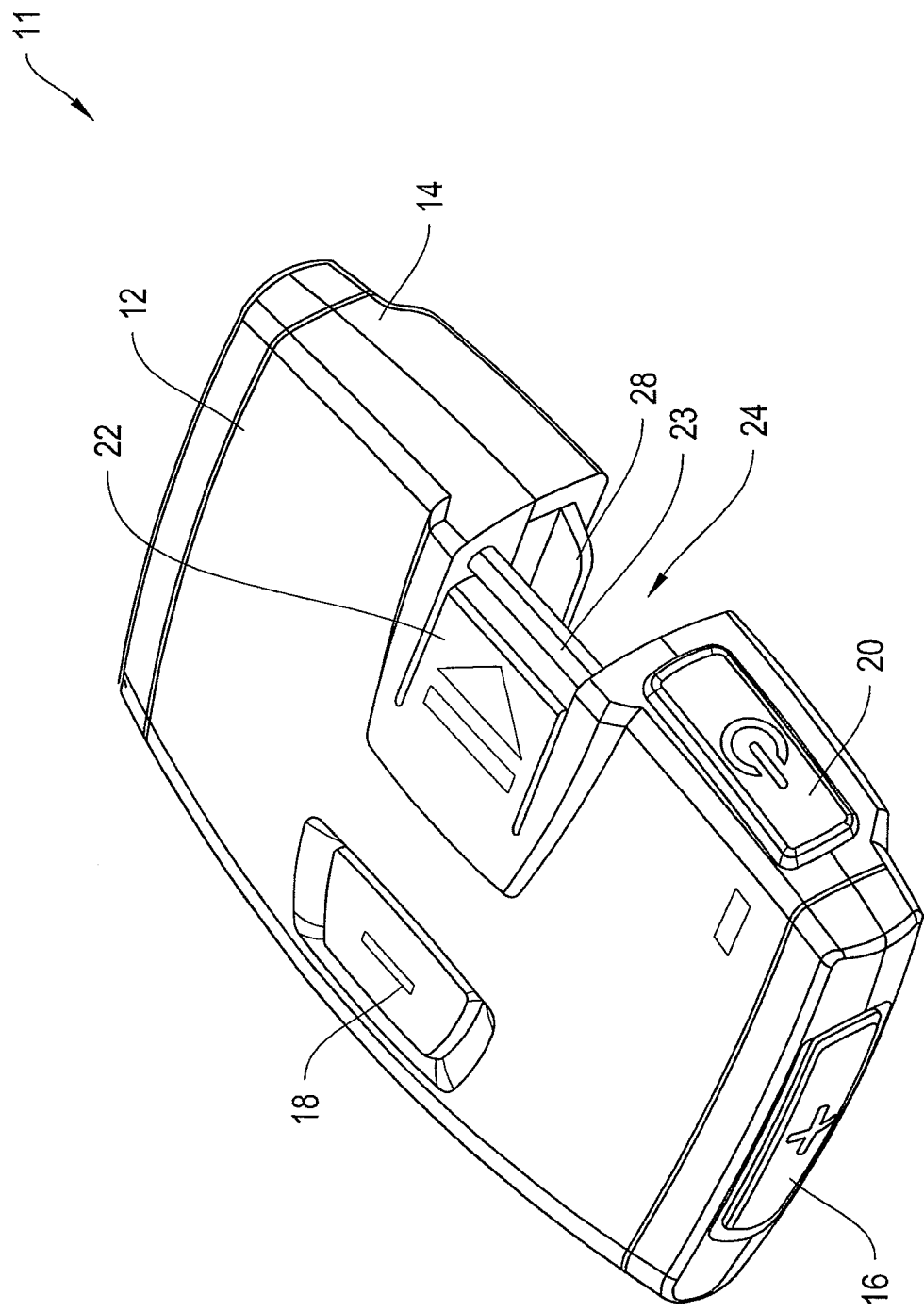
FIG. 2 is a perspective top view of the controller of the therapeutic electrical stimulation device shown in FIG. 1.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Referring now to FIG. 1, an example therapeutic electrical stimulation device 10 is shown. In this example, device 10 is a transcutaneous electrical nerve stimulation ("TENS") device. Device 10 includes controller 11 and shoe 13. Controller 11 is a device that generates electrical impulses and supplies the electrical impulses to shoe 13. Shoe 13 receives the electrical impulses from controller 11 and supplies the electrical impulses to a therapeutic location, such as the skin of a patient.

As shown in FIGS. 2-5, controller 11 includes an outer protective shell formed of upper housing 12 and lower housing 14. Upper and lower housings 12, 14 are made of any suitable material such as plastic, metal, or the like. A lower edge of upper housing 12 is configured to be connected with an upper edge of lower housing 14. In some embodiments, a fastener is used to connect upper housing 12 to lower housing 14. Examples of suitable fasteners include adhesive, screws, latching mechanisms, and other known fasteners. In other embodiments, upper housing 12 is directly connected to lower housing 14, such as by welding or over molding.

Upper and lower housings 12, 14 act together to enclose battery 26 and electrical circuitry 28. As a result, upper and lower housings 12, 14 provide protection to the enclosed components from contact with other objects that could otherwise damage the components. In some embodiments, upper and lower housings 12, 14 are water resistant to protect enclosed components from water or other fluids. Some embodiments of upper and lower housing 12, 14 are completely sealed to resist most or all fluid, gas, or particle intrusion. Some embodiments are hermetically sealed.

Battery 26 is a power source that provides electrical power to controller 11. In some embodiments, battery 26 is a rechargeable battery such as a lithium-ion battery. Battery 26 can be charged by connecting controller 11 to a battery charger, as described further below. One example of a battery charger is a docking station described in more detail herein. Inductive charging is used in some embodiments. In other embodiments, other rechargeable batteries are used, such as a nickel cadmium battery, a nickel metal hydride battery, or a rechargeable alkaline battery. Yet other embodiments include non-rechargeable, disposable batteries, such as alkaline batteries, or other known batteries. An alternate embodiment of controller 11 does not include battery 26, but rather includes a different power source such as a capacitor.

Lower housing 14 includes a controller receptacle 24 that is arranged and configured to receive a portion 42 of shoe 13. In some embodiments, lower housing 14 and portions of electrical circuitry 28 are uniquely arranged and configured to mate with portion 42 and resist mating with other shoe configurations. In addition, a railway 28 is positioned within controller receptacle 24 to receive complementary structure on show 42. These features are sometimes referred to as a keyed receptacle. One benefit of a keyed receptacle is that it can be used to resist connection with inappropriate patches or other devices, such as to resist connection with a patch that would be incompatible with controller 11. On the other hand, the keyed receptacle is also used in some embodiments to allow connection of controller 11 with various types of patches or other devices if desired.

In the example shown, the electrical circuitry 28 includes a PCB board 29 with a plurality of pins 31 extending therefrom. Pins 31 are sized to be received in receptacles formed in corresponding portion 42 of the shoe 13 to create an electrical connection between controller 11 and shoe 13, as described below.

Upper housing 12 includes a member 22 that moves into and out of controller receptacle 24 to capture and release corresponding structure on the 42 of the shoe 13. As described further below, as portion 42 is inserted into controller receptacle 24, member 22 engages structure on portion 42 to couple portion 42 to controller 11. To release portion 42, the user depresses member 22 to disengage member 22 from portion 42. Portion 42 of shoe 13 can then be pulled out of controller receptacle 24.

In one embodiment, controller 11 includes a user interface having a power button 20 and amplitude adjustment buttons 16 and 18. When power button 20 is first depressed, the controller turns ON and begins generating therapeutic electrical signals. When power button 20 is depressed again, the controller turns OFF and stops generating the therapeutic electrical signals.

While the controller 11 is ON, amplitude adjustment buttons 16 and 18 are used to adjust the amplitude of the generated therapeutic electrical signals accordingly. Amplitude adjustment button 16 provides an input to increase ("+") the amplitude of the therapeutic electrical signals. Amplitude adjustment button 18 provides an input to decrease ("−") the amplitude of the therapeutic electrical signals.

Figure 6:
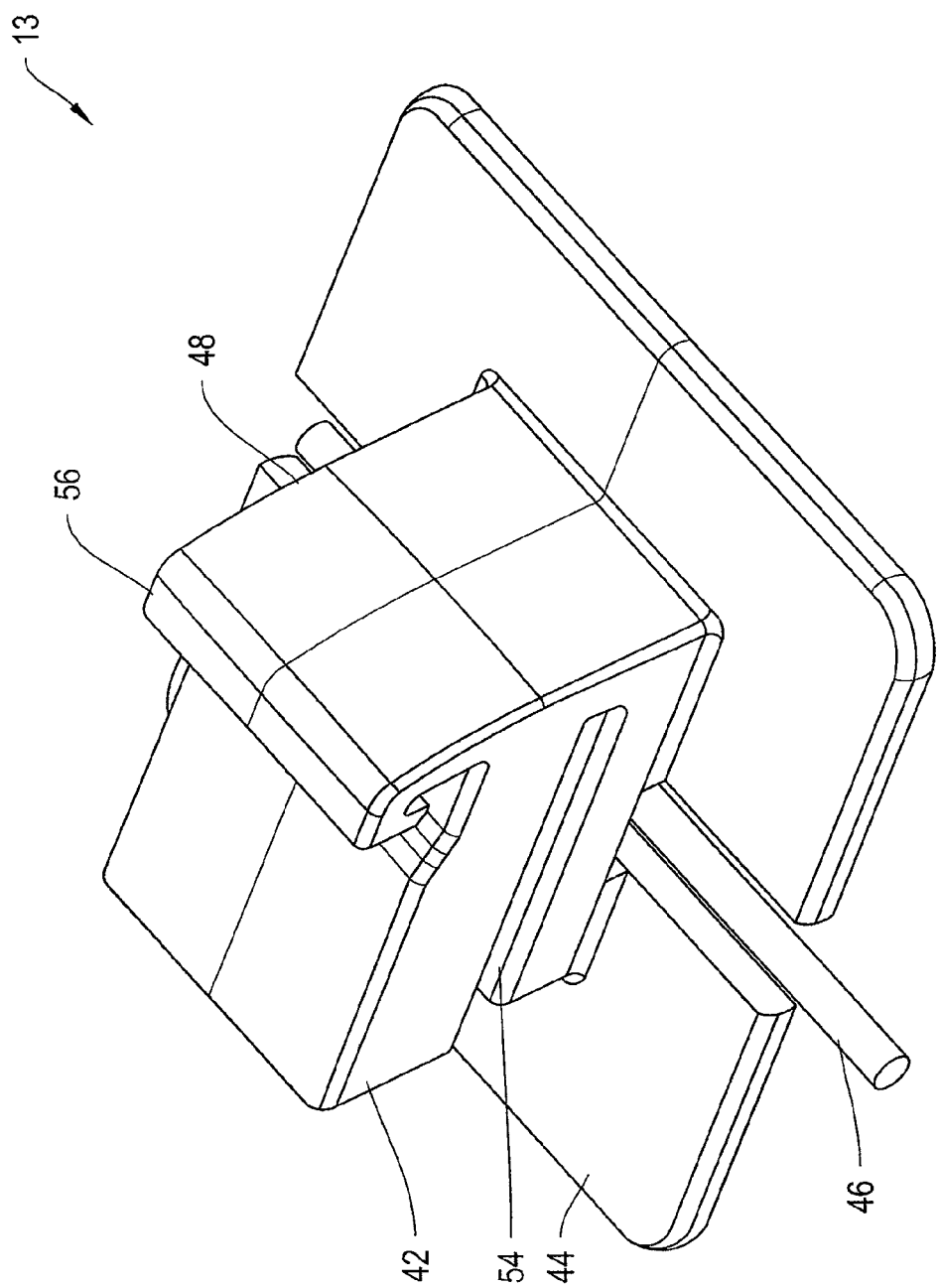
FIG. 6 is a perspective top view of a shoe of the therapeutic electrical stimulation device shown in FIG. 1.
Figure 7:
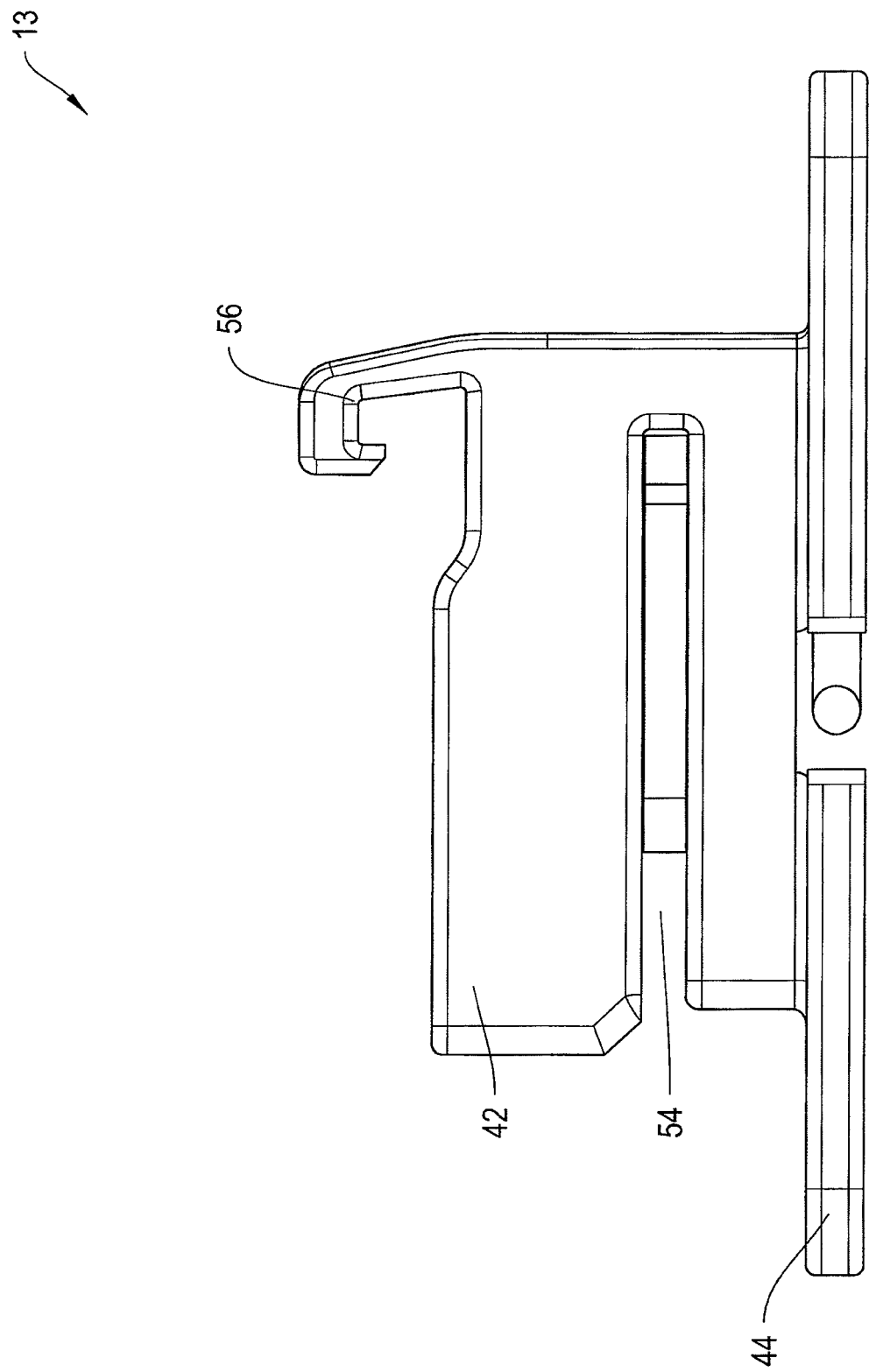
FIG. 7 is a side plan view of a shoe of the therapeutic electrical stimulation device shown in FIG. 1
Figure 8:
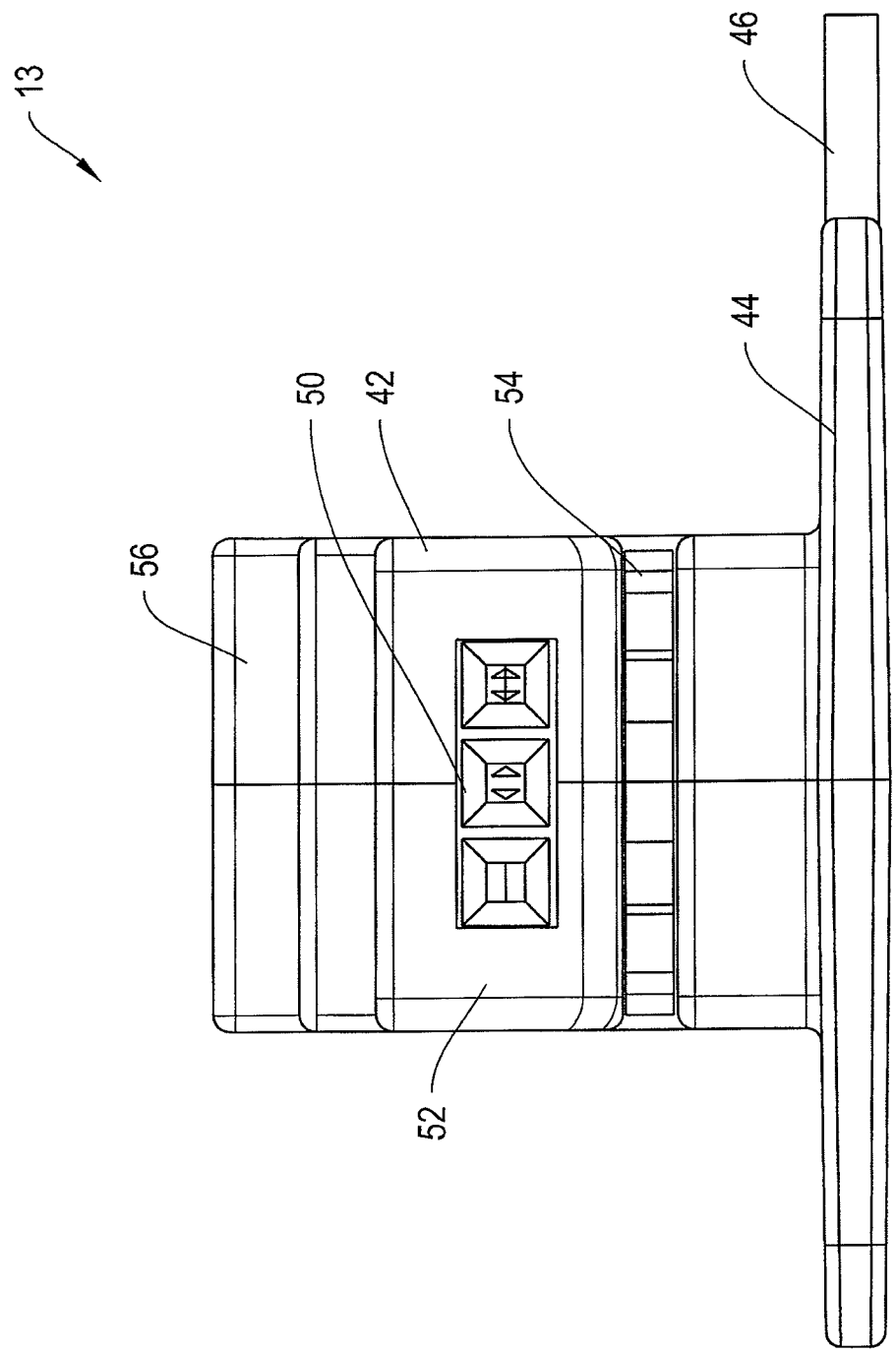
FIG. 8 is a front view of a shoe of the therapeutic electrical stimulation device shown in FIG. 1

Referring now to FIGS. 6-8, shoe 13 is shown in greater detail. In the example shown, shoe 13 includes portion 42 and a base 44. Also typically included, but not shown, is a patch with an insulating layer (see, e.g., insulating layer 122 described below). Portion 42 is configured to engage with a receptacle (shown in FIGS. 9 and 10) of controller 11. Portion 42 is a connector used to physically and electrically connect shoe 13 with controller 11.

Electrodes 46, 48 extend from show 42. Electrodes 46, 48 are typically a sheet of electrically conductive material that, when applied to a patient, provides an electrical connection with the skin of the patient to supply electrical pulses to a desired therapeutic location. An adhesive layer (not show, but see adhesive layer 128 described below) is typically applied to one side of shoe 13 to allow shoe 13 to be securely, yet removably, adhered to the skin. Some embodiments of shoe 13 include additional layers.

During stimulation, controller 11 typically generates a voltage potential between electrodes 46, 48 such that current enters the skin through one electrode, passes through the skin, and then returns through the other electrode. Some embodiments alternate the polarity of the electrodes during a therapy. In some embodiments a skin preparation product, such as a conductive gel, is applied to the skin prior to application of shoe 13.

To make electrical connection between shoe 13 and controller 11, portion 42 includes a plurality of electrical receptacles 50 on a front face 52 of portion 42. Electrical receptacles 50 are sized to receive pins 31 of controller 11 when portion 42 is fully inserted into connector receptacle 24 (see FIGS. 9 and 10). This creates an electrical connection between controller 11 and shoe 13 and allows controller 11 to deliver electrical stimulation therapy through electrodes 46, 48 to the patient.

Portion 42 defines a channel 54 sized to receive railway 28 of controller 11 when portion 42 is inserted into controller receptacle 24. Also, portion 42 includes a clip member 56 sized to engage a detent or lip 23 of member 22 of controller 11 when portion 42 is fully inserted into controller receptacle 24 to retain portion 42 within receptacle 24.

Figure 9:
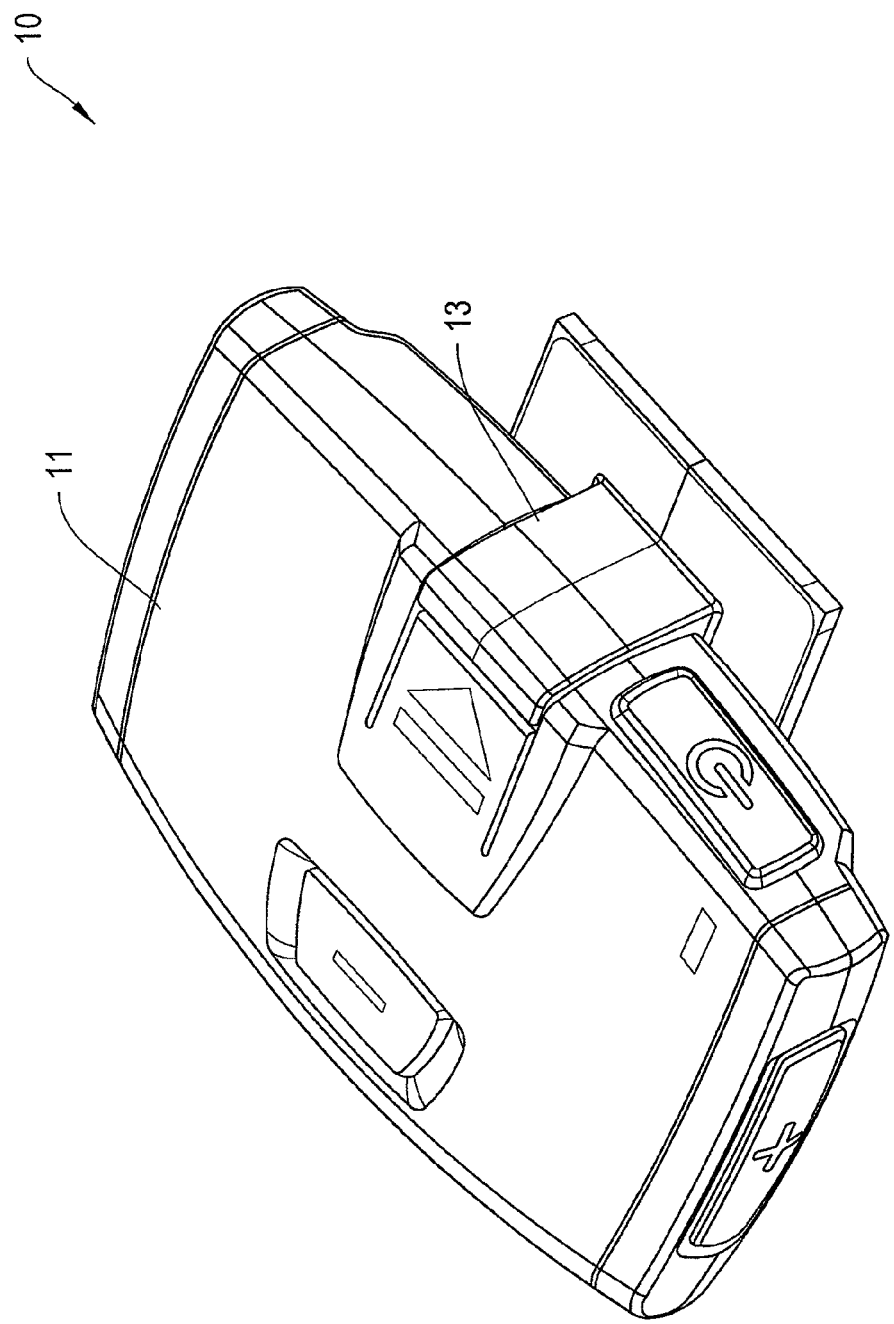
FIG. 9 is a perspective view of the therapeutic electrical stimulation device shown in FIG. 1.
Figure 10:
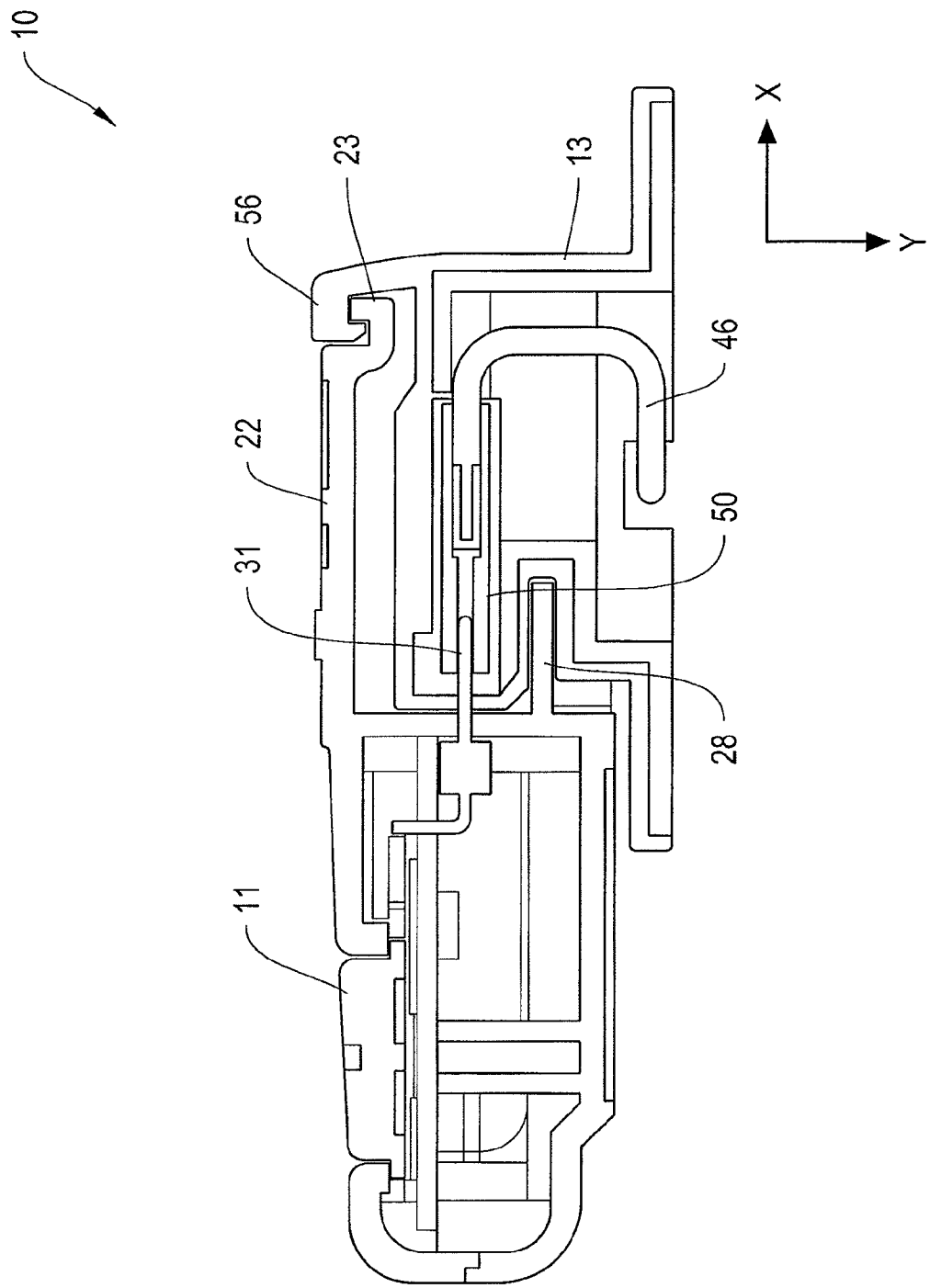
FIG. 10 is a side cross-sectional view of the therapeutic electrical stimulation device shown in FIG. 9.

Referring now to FIGS. 9 and 10, shoe 13 is coupled to controller 11. In this position, pins 31 of controller 11 are inserted into receptacles 50 of portion 42 to create an electrical connection therebetween.

In addition, railway 28 of controller 11 is received in channel 54 of portion 42 and allows portion 42 to be slid along railway 28 as portion 42 is inserted into controller receptacle 24. The engagement of railway 28 and channel 54 fixes the position of controller 11 and shoe 13 in a direction Y so that shoe 13 cannot be moved out of controller receptacle 24 in the direction Y.

Further, lip 23 of member 22 of controller 11 is engaged by clip member 56 of portion 42. The engagement of lip 23 and clip member 56 fixes the position of controller 11 and shoe 13 in a second dimension so that shoe 13 cannot be moved in a direction X out of controller receptacle 24. When the user wants to remove portion 42 from controller receptacle 24, the user depresses member 22 in the direction Y so that lip 23 clears clip member 56. Portion 42 thereupon be slid along railway 28 in direction X out of receptacle 24.

Other configurations can be used to maintain the portion 42 in the receptacle 24. For example, in another embodiment, a knob or knurl can be formed on the portion 42 that engages or is seated with a detent within the receptacle when fully inserted. When the portion 42 is removed, the knob or knurl flexes slightly to bend away from the detent so that the portion can be removed. Other configurations are possible.

In some examples described herein, shoe 13 is connected to a patch to deliver therapy to the user. In other examples, shoe 13 is connected to other structures to: (i) deliver therapy; (ii) charge controller 11; and/or (iii) program controller 11.

Figure 11:
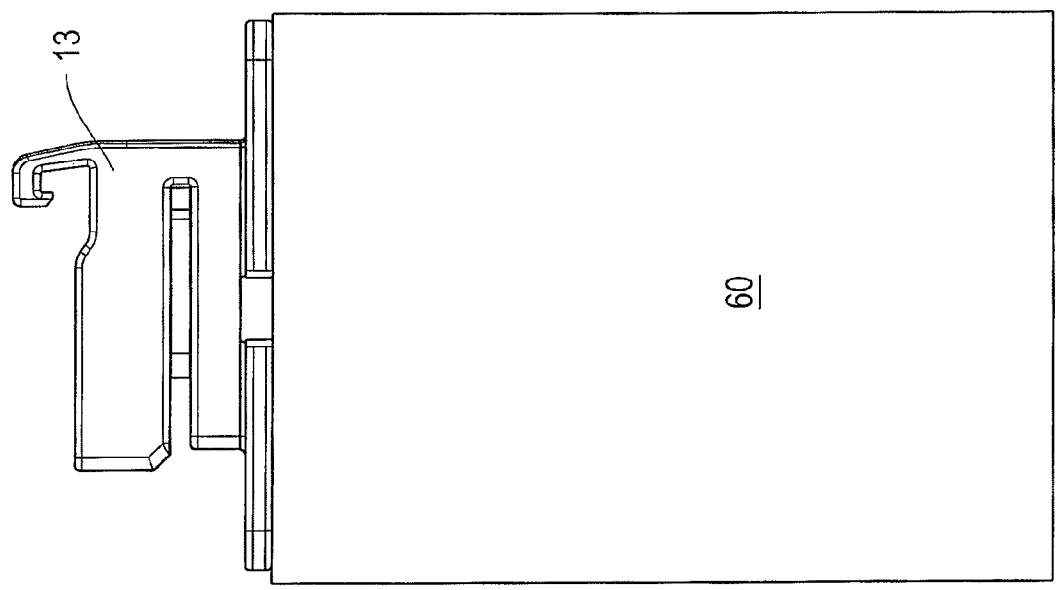
FIG. 11 is a block diagram of an example shoe of the therapeutic electrical stimulation device shown in FIG. 1 attached to a generic structure.

For example, referring now to FIG. 11, shoe 13 is electrically connected to a structure 60. As described below, shoe 13 can be connected to a plurality of different structures so that controller 11 can be coupled thereto.

In some examples, structure 60 is an apparatus that can be used to deliver therapy to the user. For example, as described below, structure 60 can be a patch (e.g., patch 104) that is attached to the skin to deliver therapy. In other examples, structure 60 is a garment such as a belt that is worn around certain anatomy of a patient, such as the waist, arm, or leg. One or more shoes 13 can be located along the best so that one or more controllers 11 can be coupled to the shoes 13 to deliver therapy at desired locations along the belt. For example, the belt can include a single shoe 13 for one controller 11, and can include a plurality of electrodes that are spaced along the belt to delivery therapy along an entire surface for the patient. In other examples, structure 60 is a brace or cast (e.g., air cast, knee brace, or back brace) with built-in electrodes that allow controller 11 to be connected to the shoe and delivery therapy to the desired area.

In some embodiments, structure 60 is electrical components that are used to provide power so that controller 11 can be connected to shoe 13 to charge battery 26 in controller 11. For example, in one embodiment, structure 60 is a docking station, such as docking station 1300 described below. In other examples, structure 60 is an electrical power transformer that can be plugged into a typical wall outlet or an automobile outlet to provide power to charge battery 26. In other examples, controller 11 can also include an auxiliary charging port, such as a USB or micro-USB port, which can be used to charge controller 11. In yet other examples, controller 11 can include on-board recharge capabilities, such as solar panels or inductive coupling technologies.

In yet other examples, structure 60 is electrical circuitry that can be used to program controller 11. In some embodiments, controller 11 includes computer readable media, such as RAM or ROM. In one embodiment, controller 11 includes flash memory that can be rewritten with new therapy programs to enhance the functionality of controller 11.

In such examples, structure 60 can be a docking station, such as docking station 1300 described below. In other examples, structure 60 can be a component in a care giver's office that allows the care giver to modify or enhance the therapies that can be provided by controller 11.

Figure 12:
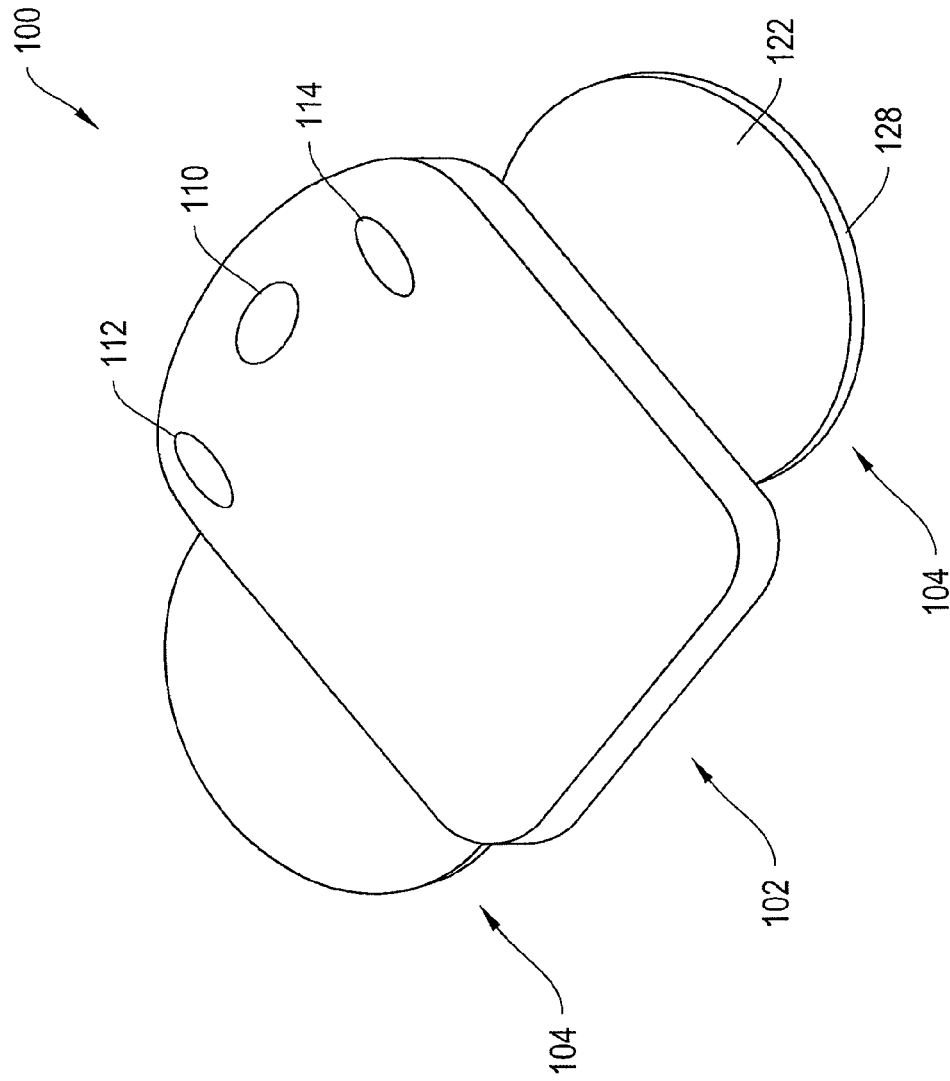
FIG. 12 is a perspective top view of another example therapeutic electrical stimulation device.

Referring now to FIG. 12, another example therapeutic electrical stimulation device 100 is shown. Device 100 is similar to device 10 described above, except that device 100 is configured differently.

In this example, device 100 is a transcutaneous electrical nerve stimulation ("TENS") device. Device 100 includes controller 102 and patch 104. Controller 102 is a device that generates electrical impulses and supplies the electrical impulses to patch 104. Patch 104 receives the electrical impulses from controller 102 and supplies the electrical impulses to a therapeutic location, such as the skin of a patient.

In one embodiment, controller 102 includes a user interface having a power button 110 and amplitude adjustment buttons 112 and 114. When power button 110 is first depressed, the controller turns ON and begins generating therapeutic electrical signals. When power button 110 is depressed again, the controller turns OFF and stops generating the therapeutic electrical signals.

While the controller 102 is ON, amplitude adjustment buttons 112 and 114 are used to adjust the amplitude of the generated therapeutic electrical signals accordingly. Amplitude adjustment button 112 provides an input to increase the amplitude of the therapeutic electrical signals. Amplitude adjustment button 114 provides an input to decrease the amplitude of the therapeutic electrical signals.

Patch 104 is typically applied to the skin of a patient. The electrical signals are conducted from the controller to the skin by patch 104. Patch 104 includes a shoe 120 (shown in FIG. 13), an insulating layer 122, and conductive electrodes 124 and 126. Shoe 120 is connected to one side of insulating layer 122, and is configured to engage with a receptacle (shown in FIG. 14) of controller 102. Shoe 120 is a connector used to physically and electrically connect patch 104 with controller 102.

Electrodes 124 and 126 (shown more clearly in FIG. 13) are located adjacent insulating layer 122 on a side opposite shoe 120. The electrodes are typically a sheet of electrically conductive material that, when applied to a patient, provides an electrical connection with the skin of the patient to supply electrical pulses to a desired therapeutic location. An adhesive layer 128 is typically applied to one side of patch 104 to allow patch 104 to be securely, yet removably, adhered to the skin. Some embodiments of patch 104 include additional layers.

During stimulation, controller 102 typically generates a voltage potential between electrodes 124 and 126 such that current enters the skin through one electrode, passes through the skin, and then returns through the other electrode. Some embodiments alternate the polarity of the electrodes during a therapy. In some embodiments a skin preparation product, such as a conductive gel, is applied to the skin prior to application of patch 104.

In some embodiments, buttons 110, 112, and 114 are arranged with a unique tactile arrangement. For example, buttons 110, 112, and 114 are arranged at one end of controller 102 and protrude out from the housing of controller 102. The tactile arrangement allows the device to be controlled by the patient or caregiver even if the device is hidden from view under clothing or in a non-visible location, such as on the back. If, for example, the device is located under a shirt on the patient's upper arm, the patient can feel controller 102 through the shirt and locate protruding buttons 110, 112, and 114. Due to the unique arrangement of buttons 110, 112, and 114, the user is able to identify each button, and select from them accordingly. Other embodiments include additional tactile elements. For example, in some embodiments buttons 110, 112, and 114 include an elevated identifier, such as a line, square, arrow, dot, circle, or Braille character. In other embodiments, buttons 110, 112, and 114 each include a unique shape, such as a square, triangle, circle, oval, rectangle, arrow, or other desired shape. In yet other embodiments, buttons are located on different locations of the housing, such as on the sides or bottom of the housing.

Figure 13:
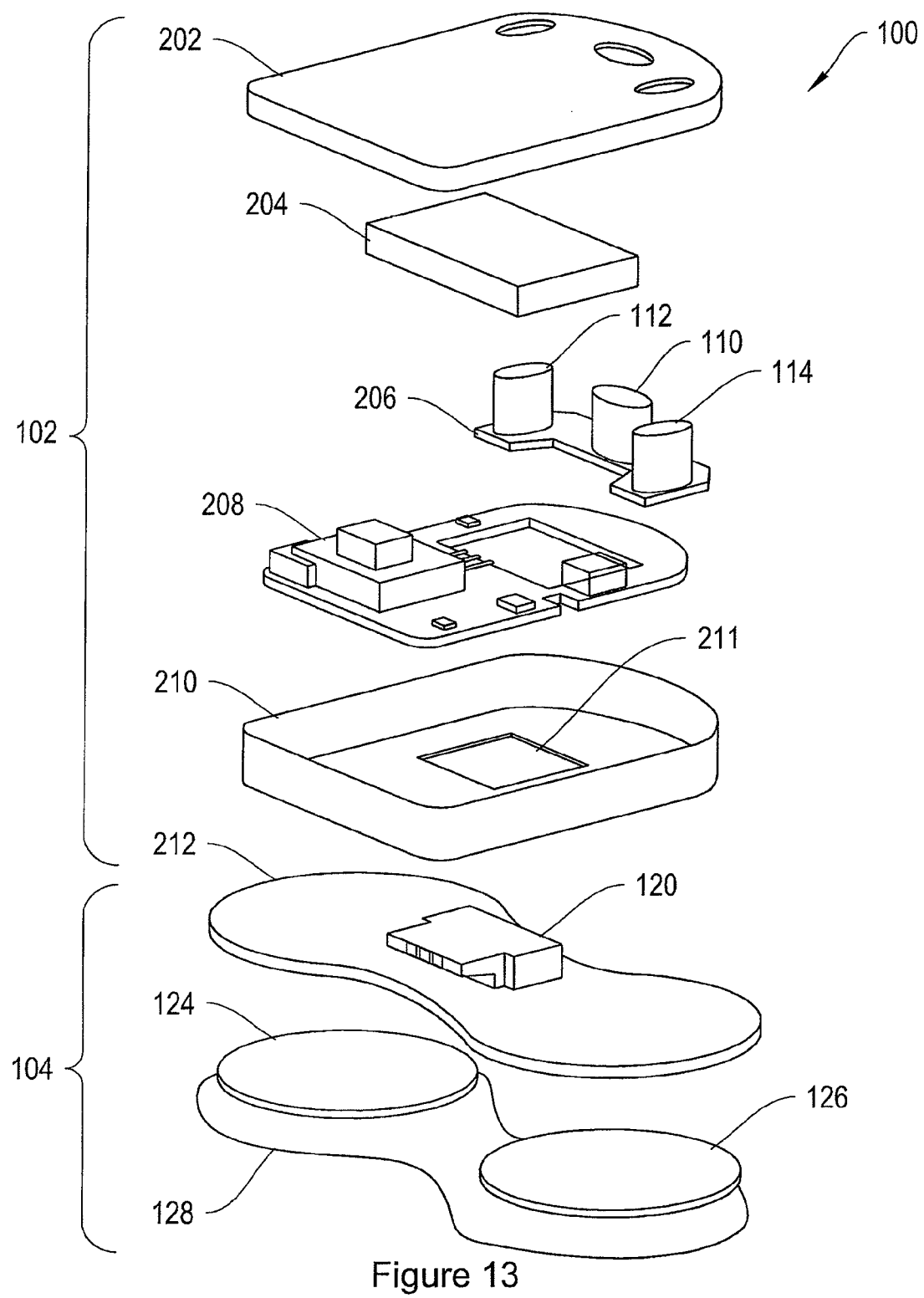
FIG. 13 is an exploded perspective view of the therapeutic electrical stimulation device shown in FIG. 12.

FIG. 13 is an exploded perspective view exemplary therapeutic electrical stimulation device 100. Device 100 includes controller 102 and patch 104. Controller 102 includes upper housing 202, battery 204, user input devices 206, electrical circuitry 208, and lower housing 210. Patch 104 includes shoe 120, insulating layer 212, electrodes 124 and 126, and adhesive layer 128.

Controller 102 includes an outer protective shell formed of upper housing 202 and lower housing 210. Upper and lower housings 202 and 210 are made of any suitable material such as plastic, metal, or the like. A lower edge of upper housing 202 is configured to be connected with an upper edge of lower housing 210. In some embodiments, a fastener is used to connect upper housing 202 to lower housing 210. Examples of suitable fasteners include adhesive, screws, latching mechanisms, and other known fasteners. In other embodiments, upper housing 202 is directly connected to lower housing 210, such as by welding or over molding.

Upper and lower housings 202 and 210 act together to enclose battery 204 and electrical circuitry 208 and to at least partially enclose user input devices 206. As a result, upper and lower housings 202 and 210 provide protection to the enclosed components from contact with other objects that could otherwise damage the components. In some embodiments, upper and lower housings 202 and 210 are water resistant to protect enclosed components from water or other fluids. Some embodiments of upper and lower housing 202 and 210 are completely sealed to resist most or all fluid, gas, or particle intrusion. Some embodiments are hermetically sealed.

Lower housing 210 includes a controller receptacle 211 that is arranged and configured to receive shoe 120 of patch 104. In some embodiments, lower housing 210 and portions of electrical circuitry 208 are uniquely arranged and configured to mate with shoe 120 and resist mating with other shoe configurations. This is sometimes referred to as a keyed receptacle. One benefit of a keyed receptacle is that it can be used to resist connection with inappropriate patches or other devices, such as to resist connection with a patch that would be incompatible with controller 102. On the other hand, the keyed receptacle is also used in some embodiments to allow connection of controller 102 with various types of patches or other devices if desired.

Battery 204 is a power source that provides electrical power to controller 102. In some embodiments, battery 204 is a rechargeable battery such as a lithium-ion battery. Battery 204 can be charged by connecting controller 102 to a battery charger. One example of a battery charger is a docking station described in more detail herein. Inductive charging is used in some embodiments. In other embodiments, other rechargeable batteries are used, such as a nickel cadmium battery, a nickel metal hydride battery, or a rechargeable alkaline battery. Yet other embodiments include non-rechargeable, disposable batteries, such as alkaline batteries, or other known batteries. An alternate embodiment of controller 102 does not include battery 204, but rather includes a different power source such as a capacitor.

User input devices 206 receive input from a user to cause controller 102 to adjust an operational mode of the device 100. User input devices 206 include power button 110 and amplitude adjustment buttons 112 and 114. User input devices 206 are arranged such that a portion of buttons 110, 112, and 114 protrude through upper housing 202. A user provides input to controller 102 by momentarily depressing one of buttons 110, 112, and 114. When the button is depressed, the force is transferred through user input device 206 to a switch of electrical circuitry 208. The switch closes to make an electrical connection and causes current flow within electrical circuitry 208. The electrical circuitry 208 responds to adjust the appropriate operational mode of controller 102.

Electrical circuitry 208 typically includes a circuit board and a plurality of electrical circuits such as a power supply circuit, pulse generator circuit, and electrical contacts for electrical connection with conductors of shoe 120. Examples of electrical circuitry 208 are described in more detail herein.

In some embodiments, electrical circuitry 208 includes sensors that receive electrical signals from patch 104. In some embodiments the electrical circuitry is activated between output pulses to monitor the patient. Some embodiments of controller 102 further include sensor electronics that monitor patch 104 to be sure that patch has not become partially or fully disconnected from the patient. If the patch does become disconnected, the electronics deactivate delivery of therapeutic electrical signals from controller 102. In some embodiments, the electronics monitor for changes in impedance between electrodes. In another embodiment, electrical circuitry 208 also includes activity monitoring, such as with an accelerometer.

Patch 104 is a device that transfers electrical impulses from controller 102 to a therapeutic location on a patient, such as the patient's skin. Patch 104 includes shoe 120, insulating layer 212, electrodes 124 and 126, and adhesive layer 128.

Shoe 120 is arranged and configured to engage with controller 102, such as through controller receptacle 211. In some embodiments, shoe 120 includes a unique configuration that is designed to mate only with controller receptacle 211 and to resist connection with other receptacles or devices. This is sometimes referred to as a keyed shoe. One benefit of a keyed shoe is that it can be used to resist connection with inappropriate controllers or other devices, such as to resist connection with a controller that would be incompatible with patch 104. On the other hand, the keyed shoe is also used in some embodiments to allow patch 104 to be connected with various types of controller 102. Shoe 120 includes conductors that conduct electrical signals between controller 102 and electrodes 124 and 126.

Patch 104 includes insulating layer 212. Insulating layer 212 is connected to patch 104 by any suitable fastening mechanism, such as adhesive, screws, nails, or other known fasteners. In other embodiments, insulating layer 212 and shoe 120 are formed of a unitary piece, such as by molding. Conductors from shoe 120 pass from shoe 120, through insulating layer 212, and are connected to electrodes 124 and 126.

In some embodiments, insulating layer 212 is a primary structural layer of patch 104. Insulating layer 212 also electrically insulates a side of patch 104. In this way, if insulating layer 212 comes into contact with a conductive object (e.g., the hand of the patient or another electronic device), insulating layer 212 prevents or at least resists the electrical conduction between electrodes 124 and 126 and the conductive object. Inadvertent electrical shocks and unintended electrical connections are thereby reduced or entirely prevented.

Electrodes 124 and 126 are electrical conductors that are used to introduce electrical signals to a therapeutic location of a patient, such as on to the patient's skin. Electrodes 124 and 126 are electrically connected to conductors that pass through shoe 120. In some embodiments electrodes 124 and 126 are generally disk-shaped to distribute the electrical signals across a relatively large area of skin. In other embodiments, electrodes 124 and 126 are of a variety of other shapes including ring-shaped, circular, elliptical, serpentine, comb-shaped, or other desired shape.

Patch 104 is connected to the skin of a patient with adhesive layer 128. In some embodiments, adhesive layer 128 is applied across an entire surface of patch 104, including across electrodes 124 and 126. In such embodiments, adhesive layer 128 is electrically conductive. In other embodiments, adhesive layer 128 is applied to the surface of patch 104, but not on the regions of electrodes 124 and 126. Other adhesive layer arrangements are used in other embodiments.

Figure 14:
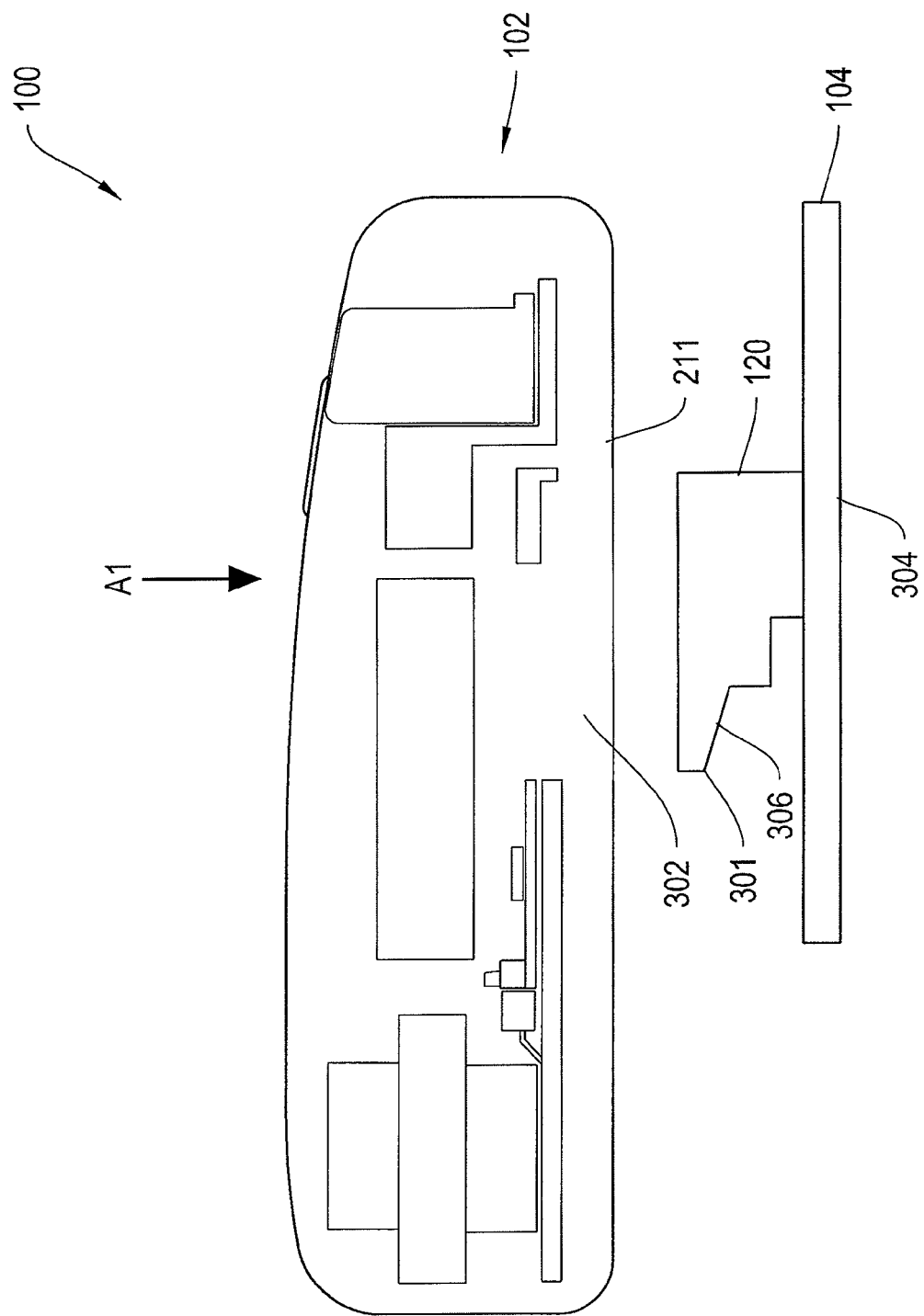
FIG. 14 is a right side cross-sectional view of the device shown in FIG. 12, including a controller that is disconnected from a patch.
Figure 15:
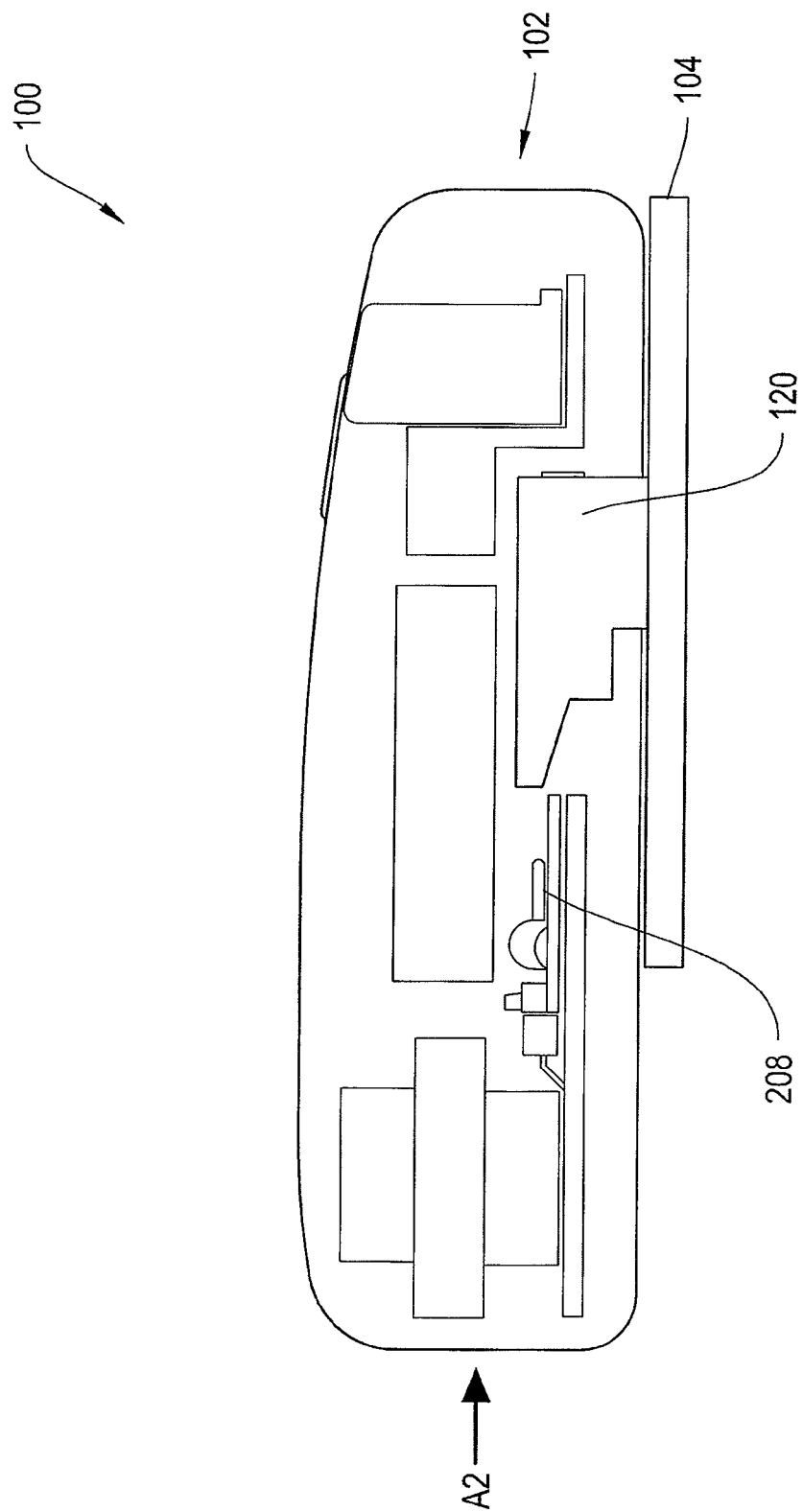
FIG. 15 is a right side cross-sectional view of the device shown in FIG. 14 with the controller being arranged over the patch.
Figure 16:
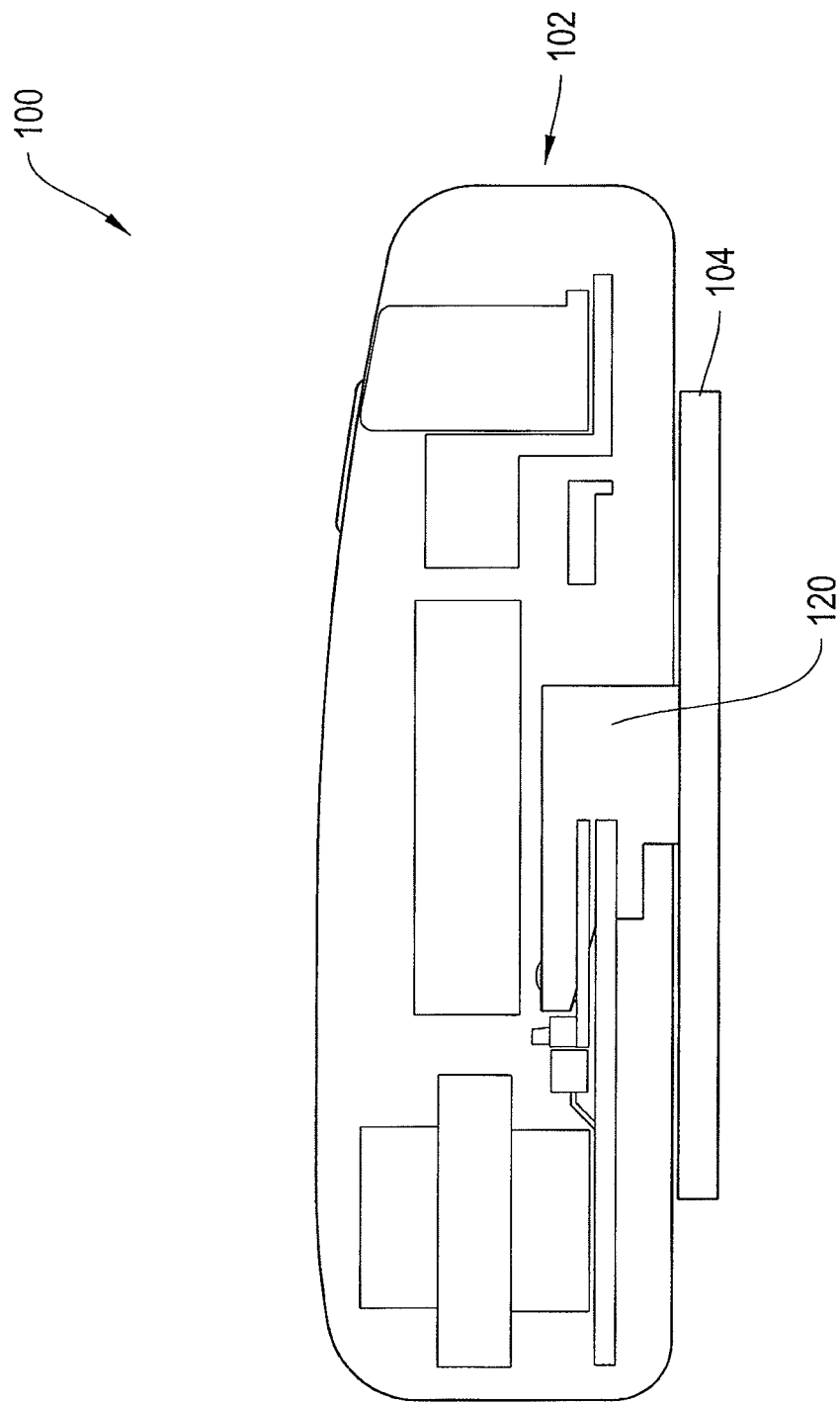
FIG. 16 is a right side cross-sectional view of the device shown in FIG. 14 with the controller being connected with the patch.

FIGS. 14-16 illustrate an exemplary method of connecting a controller 102 to a patch 104 of a therapeutic electrical stimulation device 100. FIGS. 14-16 are right side cross-sectional views of device 100. FIG. 14 illustrates controller 102 disconnected from patch 104. FIG. 15 illustrates controller 102 arranged in a first position over patch 104. FIG. 16 illustrates controller 102 arranged in a second position and connected with patch 104. A method of disconnecting controller 102 from patch 104 is the reverse of that described herein.

Before connecting controller 102 with patch 104, patch 104 is typically applied to a desired therapeutic location on the patient (not shown in FIG. 14) such that shoe 120 extends from patch 104 in a direction generally away from the therapeutic location.

The process of connecting controller 102 with patch 104 begins as illustrated in FIG. 14, such that controller 102 is arranged such that controller receptacle 211 is in line with shoe 120. Controller 102 is also oriented such that rear side 301 of shoe 120 is facing toward the rear side 302 of receptacle 211. In some embodiments, shoe 120 in receptacle 211 is shaped such that shoe 120 can only be inserted into receptacle 211 in a single orientation. In other embodiments, shoe 120 can be inserted within receptacle 211 in multiple orientations, but can only be fully engaged (as shown in FIG. 16) if shoe 120 and receptacle 211 are properly oriented.

Once properly oriented, controller 102 is moved toward patch 104 in the direction of arrow A1, such that shoe 120 enters receptacle 211 as shown in FIG. 15. Controller 102 is then advanced in the direction of arrow A2. This movement of controller 102 causes shoe 120 to engage with controller 102 as shown in FIG. 16. In particular, electrical circuitry 208 makes electrical contact with conductors of shoe 120 to electrically connect electrodes of patch 104 with electrical circuitry 208.

Electrical connectors are used to electrically connect conductors of shoe 120 with electrical circuitry 208. In one embodiments, male and female plug-type connectors are included as part of shoe 120 and electrical circuitry 208. In another embodiment, surface conductors are used to connect with protruding electrical contacts, such as used in Universal Serial Bus (USB) connectors and for connecting memory cards with memory slots. Other electrical connectors are used in other embodiments.

As described above, FIGS. 14-16 illustrate a two-step method of connecting patch 104 and controller 102. The first step involves moving controller 102 in the direction of arrow A1, and the second step involves moving controller 102 in the direction of arrow A2. This method of connection is partially a result of the "L-shape" of shoe 120. Shoe 120 has a first portion 304 that extends generally normal to a surface of insulating layer 212, and a second portion 306 that extends at generally a right-angle to the first portion 304.

One of the benefits of this shape of shoe 120 is that it resists unintentional disengagement of controller 102 from patch 104, once controller 102 is properly connected (as shown in FIG. 16). For example, if a force is applied to controller 102 in a direction opposite arrow A1, the second portion of shoe 120 resists disengagement of controller 102 from patch 104. Sideways forces (e.g., forces normal to arrow A1 and arrow A2) are also resisted, as well as a force in the direction of arrow A2. A force in the direction opposite arrow A2 will result in disconnection of shoe 120 from electrical circuitry 208. However, shoe 120 will still provide support to receptacle 211 unless controller 102 is arranged vertically below patch 104. This allows the user to manually grasp controller 102 before it becomes completely disconnected from patch 120 and reconnect controller 102, if desired. If controller 102 is arranged vertically below patch 104, then gravity will tend to pull controller 102 away from patch 104.

In another embodiment, shoe 120 has a generally linear shape (not shown in FIGS. 14-16), such that shoe 120 is plugged directly into controller 102 in a single step, namely the insertion of shoe 120 into receptacle 211. In this embodiment, electrical circuitry 208 includes an electrical connector that is in line with the path of entry of shoe 120 into receptacle 211 or directly surrounds the point of entry.

In another possible embodiment, shoe 120 has an "L-shape" but receptacle 211 is arranged on a side of controller 102. In this embodiment, connection of controller 102 with patch 104 is accomplished in a single step—insertion of a second portion of shoe 104 into the side receptacle.

Some embodiments of shoe 120 and receptacle 211 are arranged and configured to safely disconnect from each other upon the application of a sufficient force. If the user bumps device 100 on another object, for example, it is preferred that controller 102 electrically disconnects from patch 104 before patch 104 becomes disengaged from the patient. Shoe 120 and receptacle 211 are designed to remain connected unless a sufficient force is applied to controller 102 and before the force becomes large enough to disconnect patch 104 from the patient.

Figure 17:
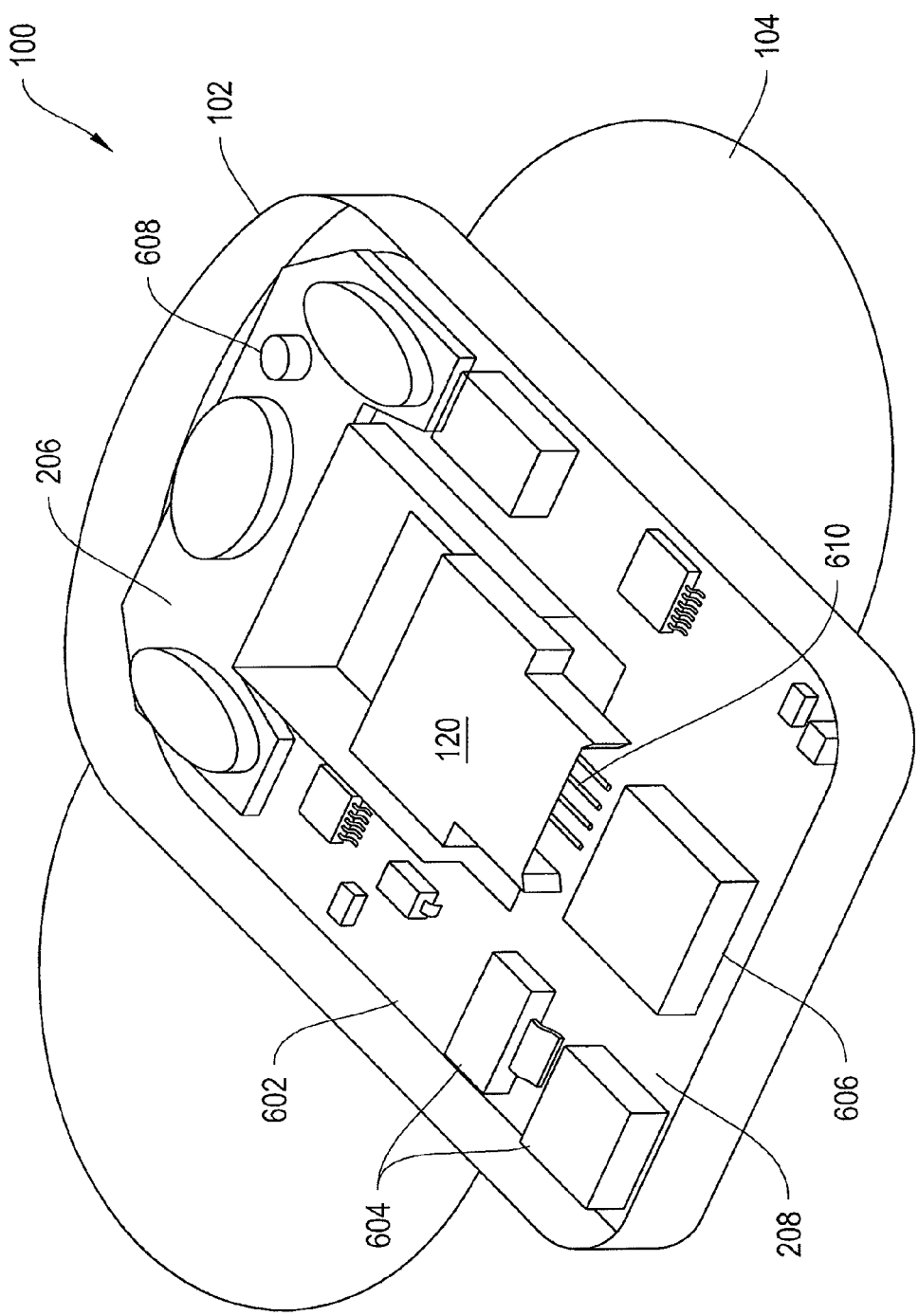
FIG. 17 is a perspective top view of the device shown in FIG. 12 in a partially assembled configuration.

FIG. 17 is a perspective top view of an exemplary embodiment of partially assembled device 100. In this figure, upper housing 202 and battery 204 (shown in FIG. 13) are removed. Device 100 includes controller 102 and patch 104. Controller 102 includes user input device 206 and electrical circuitry 208. Electrical circuitry 208 includes circuit board 602 and electronic components 604. Electrical components 604 include transformer 606, status indicator 608, and electrical connector 610.

In FIG. 17, shoe 120 is shown in the fully connected position, such as shown in FIG. 16. When in this position, electrical connectors of shoe 120 mate with electrical connectors 610 of electrical circuitry 208. Circuit board traces on or within circuit board 602 communicate electrical signals between electrical components 604 and shoe 120.

Some embodiments of electrical circuitry 208 include transformer 606. In some embodiments (such as shown in FIG. 13), the transformer is mounted on a surface of the circuit board. To reduce space consumed by transformer 606, some embodiments include a hole in circuit board 602. Transformer 606 is inserted within the hole to reduce the overall distance that transformer 606 extends above circuit board 602. This allows upper and lower housing 202 and 210 to have a reduced profile.

Some embodiments include one or more status indicators 608. Status indicators inform a user of the operational status of device 100 and can come in the form of visual, audible, and/or tactile indicators. Examples of suitable status indicators 608 include a light, an LED, a liquid crystal or other type of display, a speaker, a buzzer, and a vibrator. Status indicators 608 are used in some embodiments to show whether device 100 is ON or OFF. In other embodiments, status indicators 608 communicate an operational mode, such as a type of therapy being provided, or a change in operational mode, such as an increase or decrease in amplitude. In yet other embodiments, status indicators 608 are used to show battery power status (e.g., full power, percentage of full power, or low on power/in need of charge), or charging status (e.g., charging or fully charged). Other indicators are used in other possible embodiments. Speakers, buzzers, and vibrators are particularly useful for those with certain disabilities or impairments and also for communication when the device is located in an area that is not easily visible (e.g., on the back of a patient).

Figure 18:
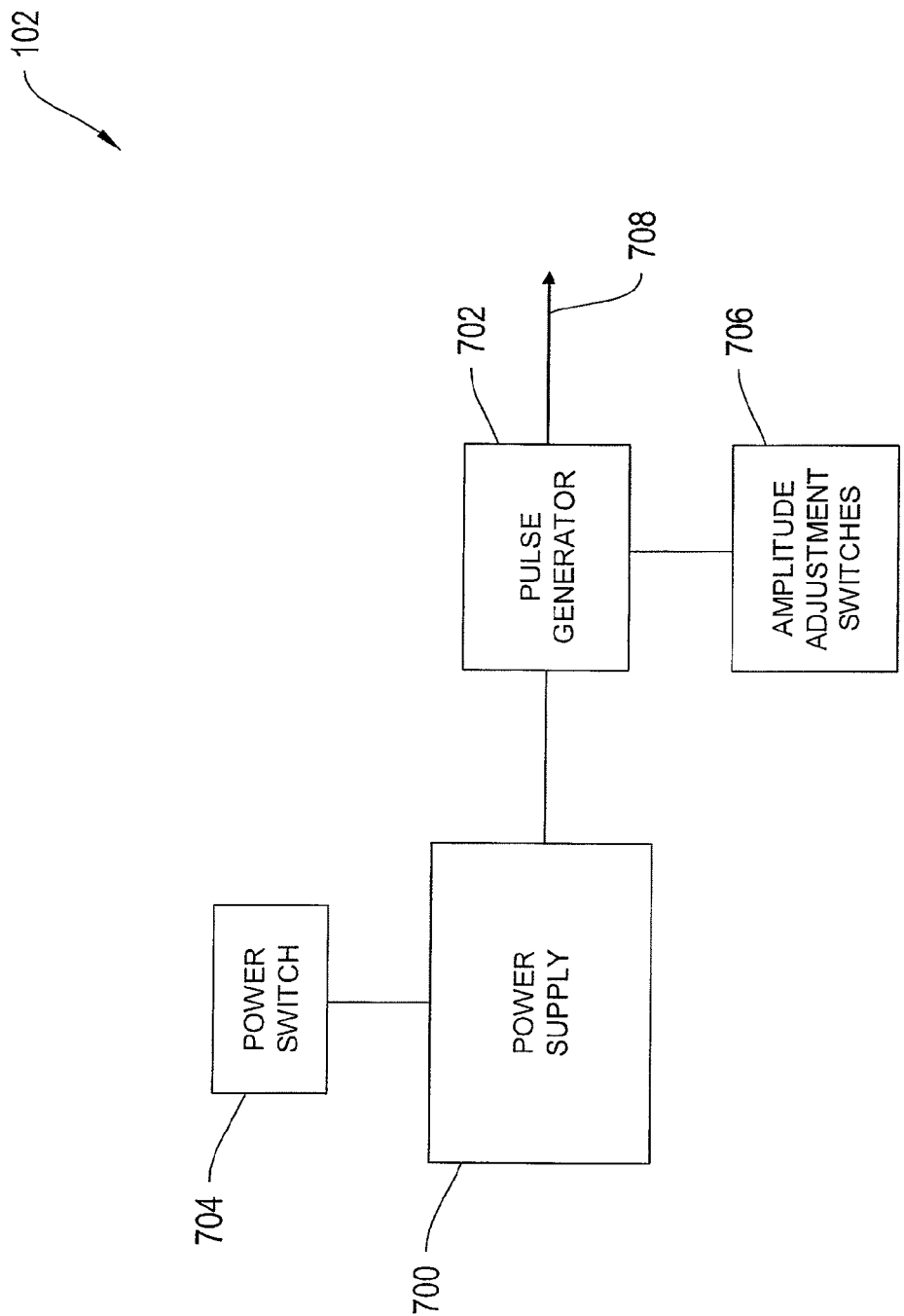
FIG. 18 is a block diagram of an electrical schematic for the controller shown in FIG. 14.

FIG. 18 is a block diagram of an exemplary electrical schematic for controller 102. Controller 102 includes power supply 700, pulse generator 702, power switch 704, amplitude adjustment switches 706, and output 708.

Power supply 700 provides electrical power to controller 102. In some embodiments, power supply 700 includes a battery and also includes power filtering and/or voltage adjustment circuitry. Power supply 700 is electrically coupled to power switch 704 and to pulse generator 702. Power switch 704 receives input from a user through power button 110 (e.g., shown in FIG. 12) and operates with power supply 700 to turn controller 102 ON or OFF.

Pulse generator 702 generates therapeutic electrical signals. Pulse generator 702 is electrically coupled to output 708 and provides the electrical signals to output 708. In turn, output 708 is electrically coupled to patch electrodes to deliver the electrical signals to the therapeutic location of the patient. Amplitude adjustment switches 706 are electrically coupled to pulse generator 702 and receive input from the user through amplitude adjustment buttons 112 and 114 (e.g., shown in FIG. 12). Amplitude adjustment switches 706 operate with pulse generator 702 to adjust the intensity of the electrical signals sent to output 708.

Some examples of suitable pulse generators are described in U.S. Pat. Nos. 4,887,603 and 4,922,908, both by Morawetz et al. and titled MEDICAL STIMULATOR WITH STIMULATION SIGNAL CHARACTERISTICS MODULATED AS A FUNCTION OF STIMULATION SIGNAL FREQUENCY, the disclosure of which is hereby incorporated by reference in its entirety. In some embodiments, the electrical signals generated by pulse generator 702 are simple modulated pulse (SMP) signals. Other configurations and electrical signals are possible.

Figures 1, 19:
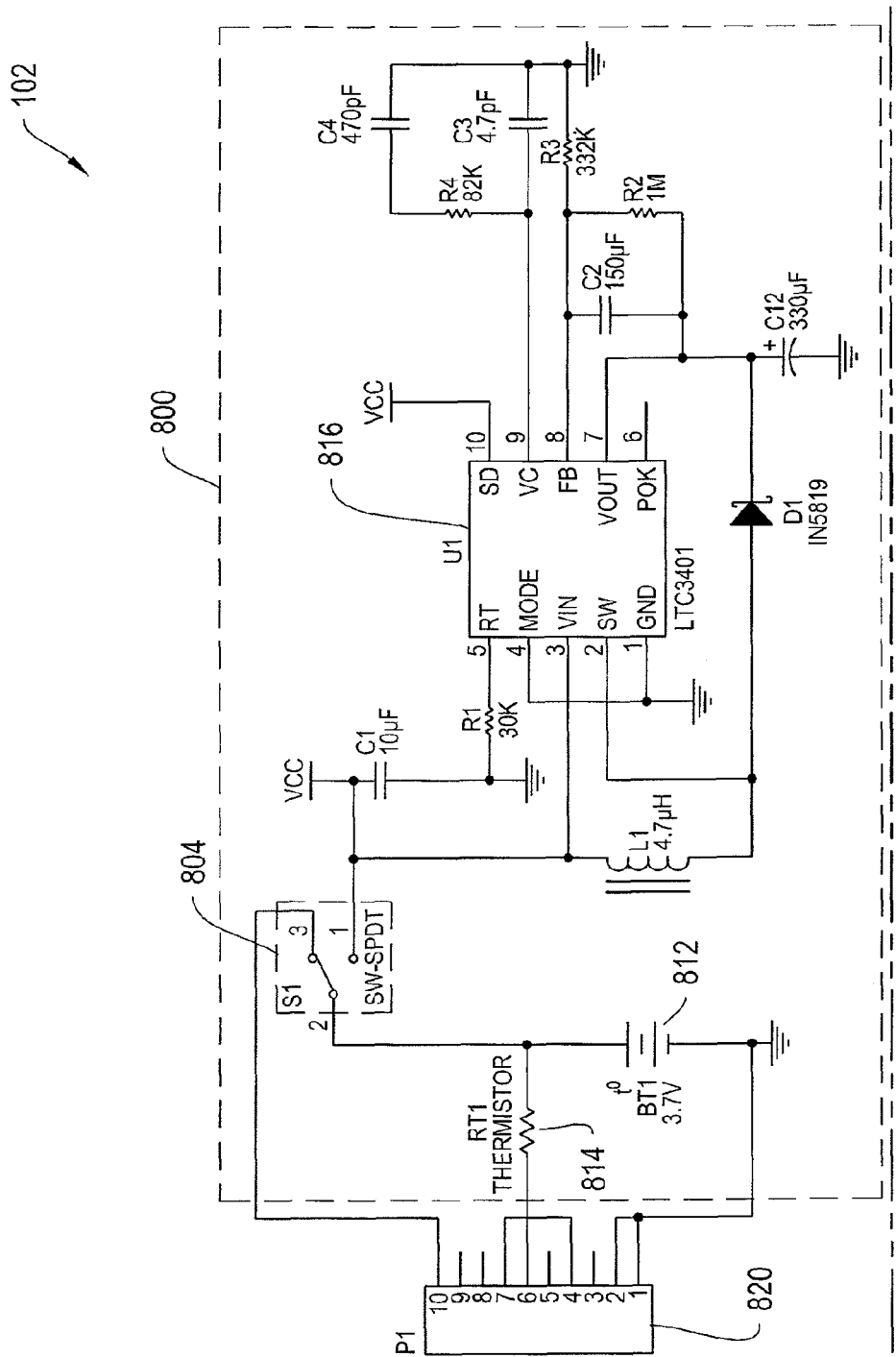
FIG. 19 is an electrical schematic of an exemplary circuit for the controller shown in FIG. 14.
Figures 2, 19:
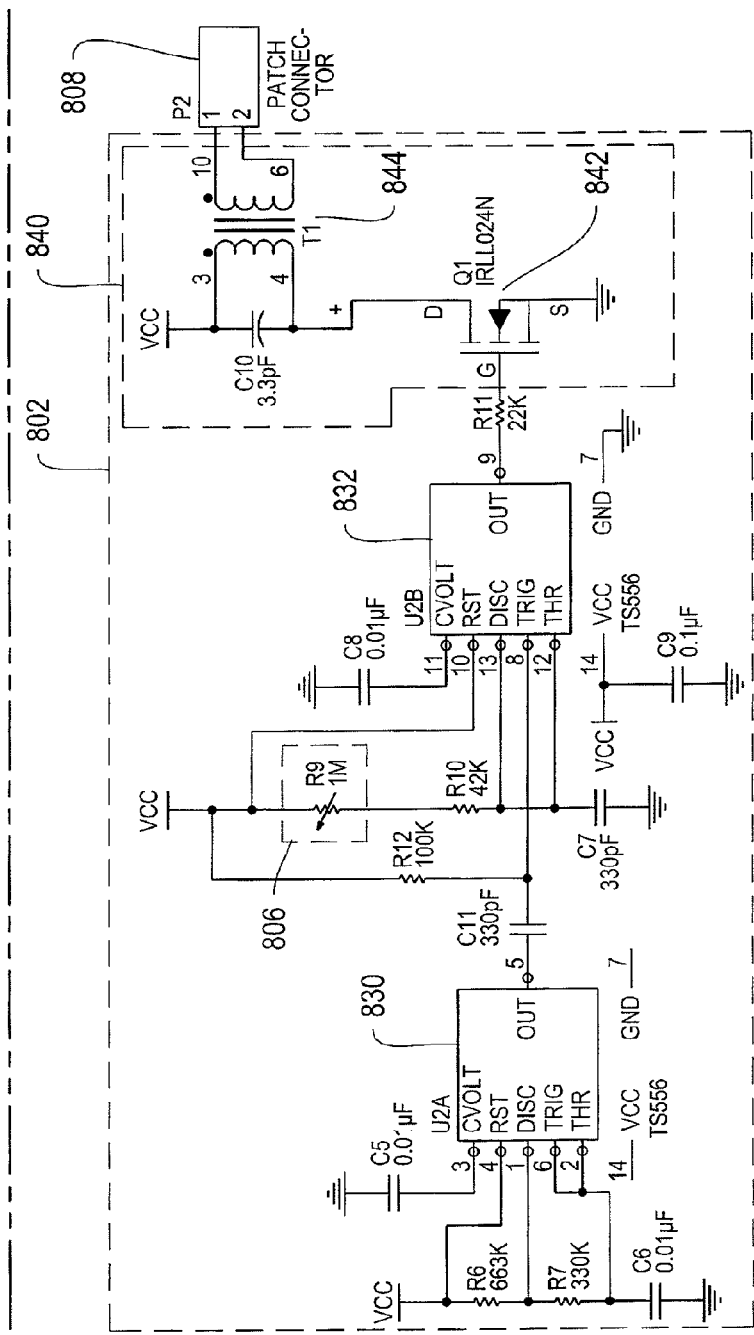

FIG. 19 is an electrical schematic of an exemplary circuit for controller 102. Controller 102 includes power supply 800, pulse generator 802, power switch 804, amplitude adjustment switch 806, and output 808. Power supply 800 includes battery 812, thermistor 814, step up converter 816, and other electrical components. Power supply 800 is electrically coupled to supply power to pulse generator 802. In addition, power supply 804 is electrically coupled to connector block 820 that is used to supply power to power supply 800 to charge battery 812.

In this example, battery 812 is a lithium-ion battery having a voltage of about 3.7 to 4.2 volts, although other battery types and voltages are used in other embodiments. Thermistor 814 is electrically coupled between battery 812 and connector block 820 and is used to detect the temperature of battery 812 to ensure that battery 812 is not overheated while recharging. Power switch 804 is used to turn controller 102 ON or OFF. In one embodiment, switch 804 is a single pole double throw (SPDT) switch, as shown. Power supply 800 also includes step up converter 816. Step up converter 816 operates to increase the voltage of power from battery 812 to a desired voltage. One suitable step up converter is the LTC3401 micropower synchronous boost converter that is distributed by Linear Technology Corporation, with headquarters in Milpitas, Calif.

Pulse generator 802 receives power from power supply 700 and generates a therapeutic electrical signal. The therapeutic electrical signal is provided to by pulse generator 802 to output 808. Pulse generator 802 includes amplitude adjustment switch 806. In this embodiment, amplitude adjustment switch 806 is a potentiometer. When the potentiometer is adjusted, intensity of the electrical signal generated by pulse generator 802 is increased or decreased accordingly.

In this example, pulse generator 802 includes first and second timers 830 and 832 as well as additional circuitry as shown. In one embodiment, both timers 830 and 832 are the TS556 low-power dual CMOS timer, distributed by STMicroelectronics, with headquarters in Geneva, Switzerland.

Pulse generator 802 also includes output stage 840. Output stage 840 includes MOSFET 842 and transformer 844. Output stage 840 acts to increase the output voltage of the electrical signal before sending the electrical signal to output 808.

Figures 1, 20:
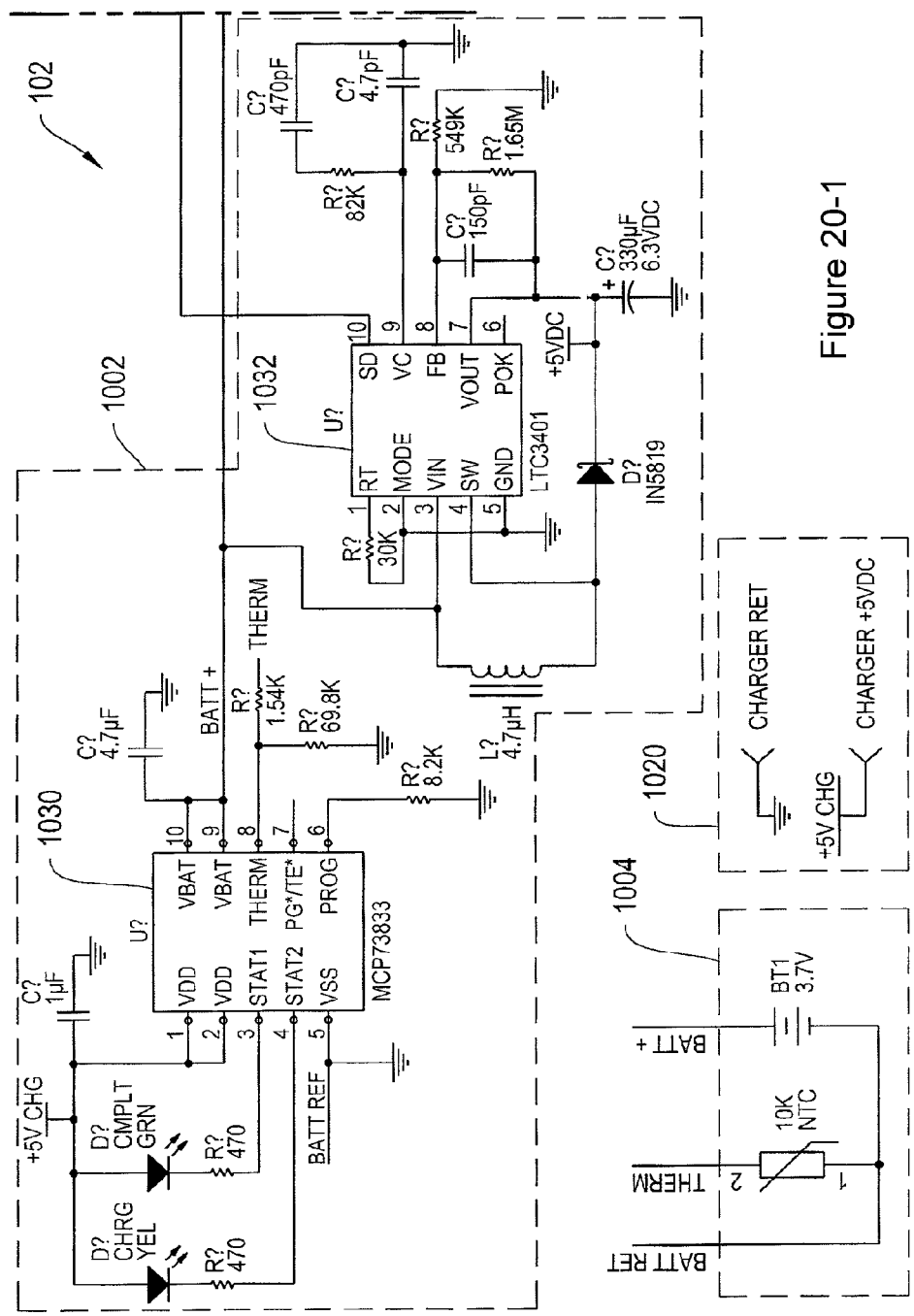
FIG. 20 is another block diagram of an electrical schematic for the controller shown in FIG. 14.
Figures 2, 20:
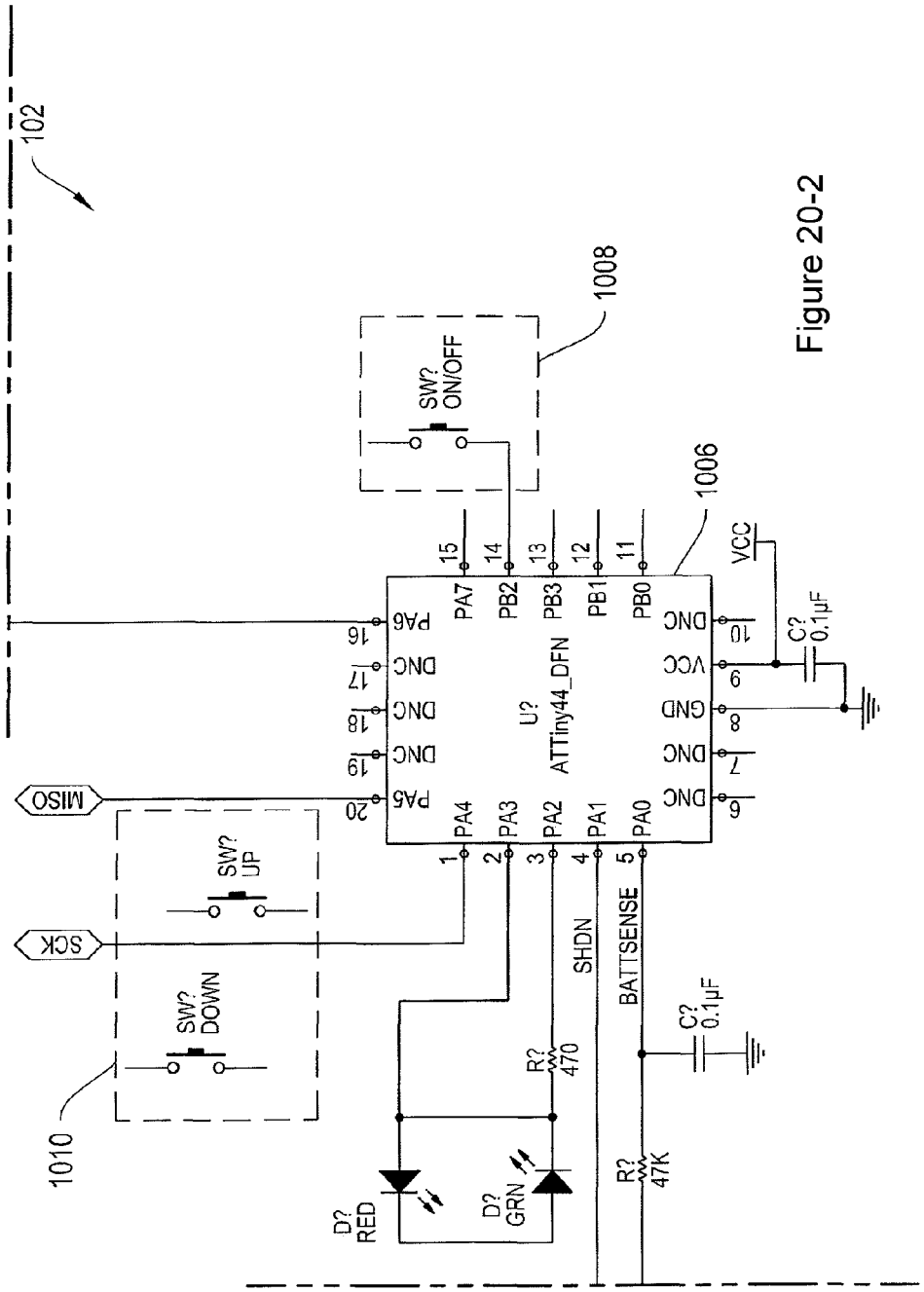
Figures 3, 20:
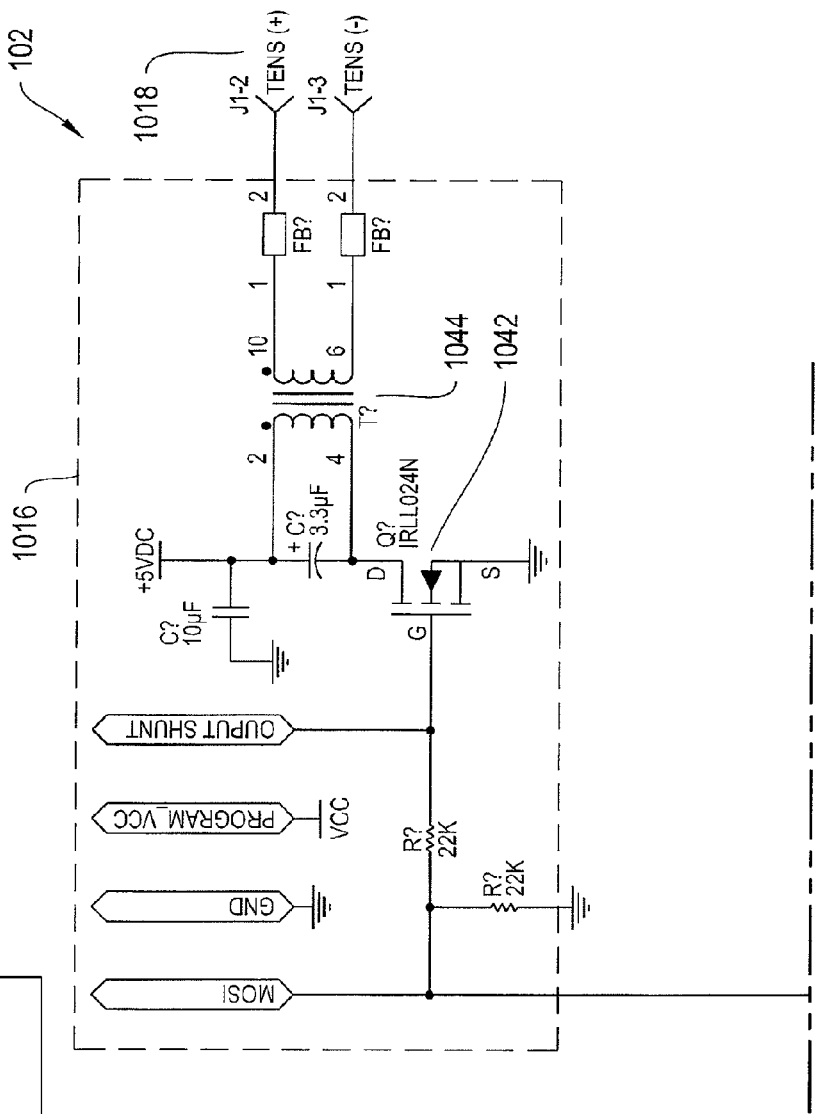

FIG. 20 is a block diagram of another exemplary electrical schematic for controller 102. In this embodiment, controller 102 is formed from primarily digital circuitry. Controller 102 includes power supply 902, battery 904, controller processor 906, power switch 108, amplitude adjustment switches 910, data communication device 912, data storage device 914, output stage 916, and output 918. Controller 102 can be connected to external power source 920, such as to charge battery 904. In one embodiment, external power source 920 is a home or commercial power supply, such as available through an electrical power outlet. In another embodiment, external power source 920 is an vehicle power supply, such as accessible through a 12V receptacle.

During normal operation, power supply 902 receives power from battery 904. Power supply 902 converts the battery power to a desired voltage before supplying the power to other components of controller 102. Power supply 902 also includes battery charger 930. Battery charger 930 receives power from an external power supply and operates to recharge battery 904.

Control processor 906 controls the operation of controller 102. Control processor 906 is powered by power supply 902. Control processor 906 also generates electrical signals that are provided to output stage 916.

Control processor 906 is electrically coupled to power switch 908 and amplitude adjustment switches 910. Control processor 906 monitors the state of power switch 908. When control processor 906 detects that the state of power switch 908 has changed, control processor 906 turns controller 102 ON or OFF accordingly. Control processor 906 also monitors the state of amplitude adjustment switches 910. When control processor 906 detects that the state of amplitude adjustment switches 910 has changed, control processor 906 increases or decreases the intensity of electrical signals provided to output stage 916 accordingly.

Control processor 906 includes memory 932. Firmware 934 is stored in memory 932. Firmware 934 includes software commands that are executed by control processor 906 and defines logical operations performed by control processor 906.

In some embodiments, controller 102 includes a data communication device 912. Data communication devices include wired or wireless communication devices, such as serial bus communication devices (e.g., a Universal Serial Bus communication devices), local area networking communication devices (e.g., an Ethernet communication device), a modem, a wireless area networking communication device (e.g., an 802.11x communication device), a wireless personal area networking device (e.g., a Bluetooth™ communication device), or other communication device.

Data communication device 912 can be used to send and receive data with another device. For example, data communication device 912 can be used to download different firmware 934 to alter the operation of control processor 906. Data communication device 912 can also be used to upload data to another device. For example, control processor 906 stores a therapy log in data storage device 914. The control processor 906 can be used to upload the therapy log to an external device by sending the data log to data communication device 912.

Data storage device is a device capable of storing data, such as a memory card or other known data storage device. In some embodiments, data storage device 914 is part of memory 932.

When controller 102 is ON, control processor 906 generates therapeutic electrical signals, and provides those signals to output stage 916. Output stage 916 converts and filters the electrical signals, and then provides the electrical signals to output 918. Output 918 is electrically coupled to a patch that delivers electrical signals to the patient.

Figures 1, 21:
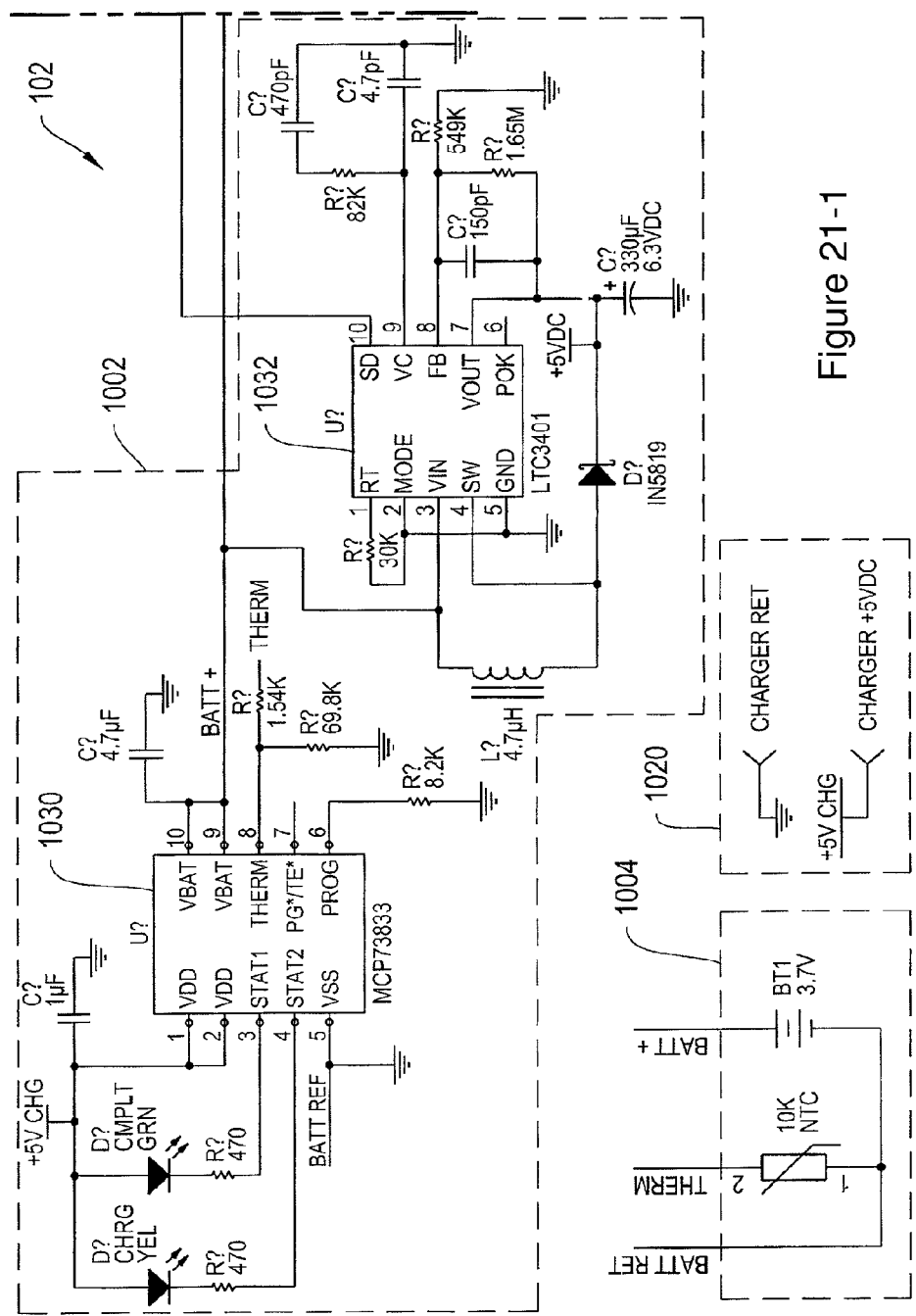
FIG. 21 is another electrical schematic of an exemplary circuit for the controller shown in FIG. 14.
Figures 2, 21:
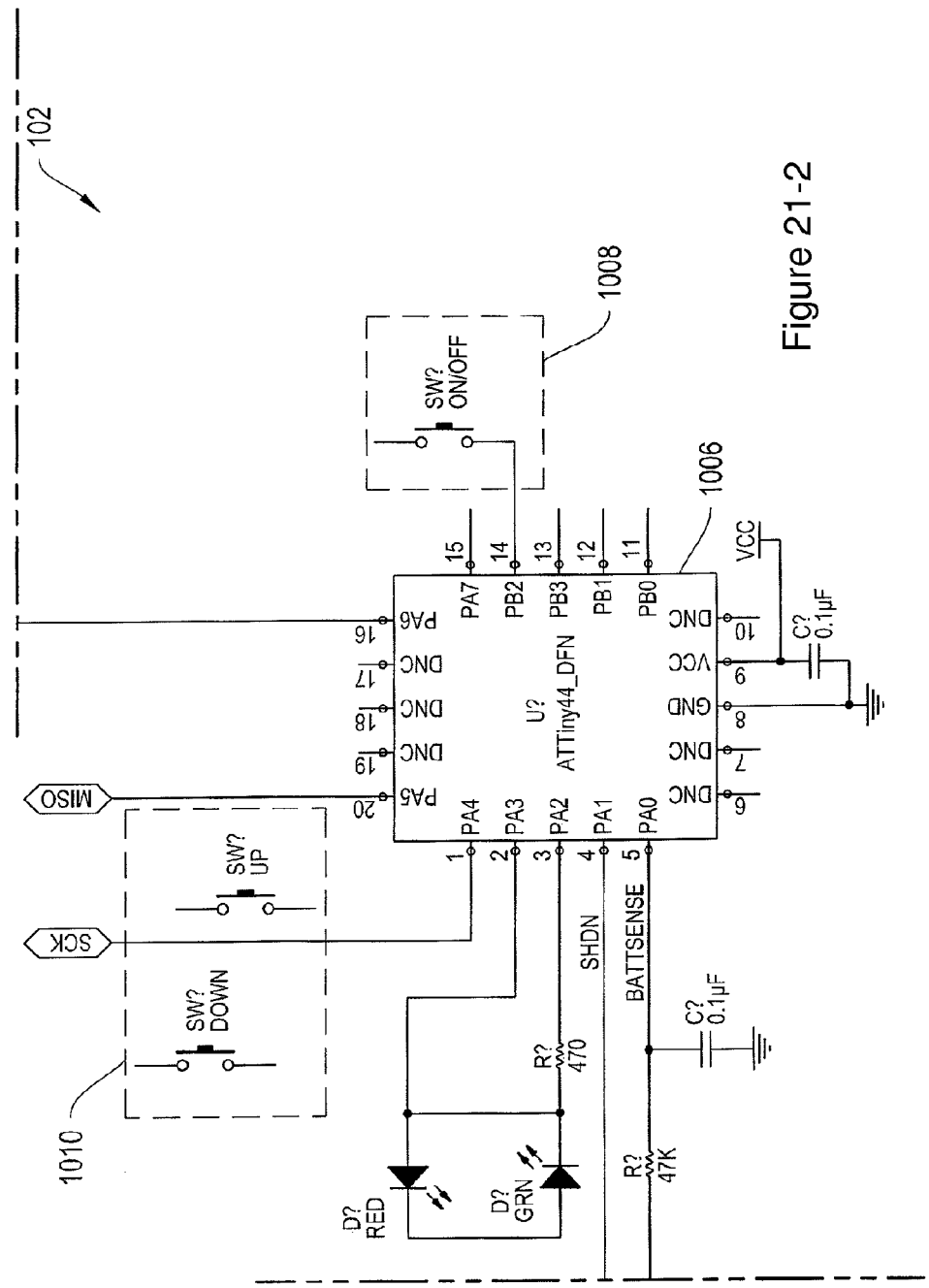
Figures 3, 21:
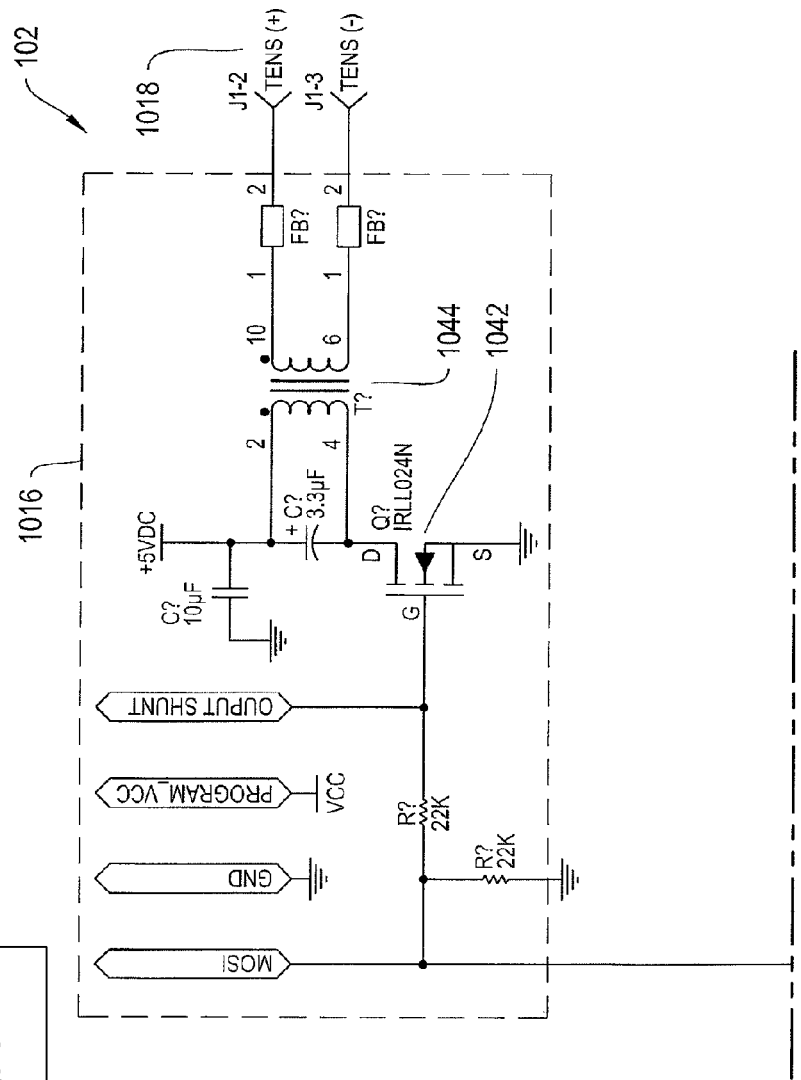

FIG. 21 is an electrical schematic of another exemplary circuit for controller 102. In this embodiment, controller 102 includes a control processor 1006 that controls the operation of controller 102. In this embodiment, controller 102 is made from primarily digital circuitry. Controller 102 includes power supply 1002, battery 1004, control processor 1006, power switch 1008, amplitude adjustment switches 1010, output stage 1016, and output 1018. Controller 102 can also be connected to external power source 1020, such as to charge battery 1004.

In this embodiment, power supply 1002 includes a lithium-ion charge management controller 1030 and a step up converter 1032, as well as other electrical components as shown. An example of a suitable lithium-ion charge management controller 1030 is the MCP73833 stand-alone linear lithium-ion charge management controller manufactured by Microchip Technology Inc., of Chandler, Ariz. An example of a suitable step up converter is the LTC3401 micropower synchronous boost converter.

Battery 1004 provides power to power supply 1002. In this example, battery 1004 is a lithium-ion 3.7V battery. Power supply 1002 can also be connected to external power source 1020, such as a 5V DC power source. External power source 1020 provides power to power supply 1002 that enables power supply 1002 to recharge battery 1004. In some embodiments, battery 1004 includes a thermistor to monitor the temperature of battery 1004 during charging.

Control processor 1006 controls the operation of controller 102. One example of a suitable control processor 1006 is the ATtiny44 8-bit microcontroller manufactured by Amtel Corporation, located in San Jose, Calif. Alternatively, various other processing devices may also be used including other microprocessors, central processing units (CPUs), microcontrollers, programmable logic devices, field programmable gate arrays, digital signal processing (DSP) devices, and the like. Control processor 1006 may be of any general variety such as reduced instruction set computing (RISC) devices, complex instruction set computing devices (CISC), or specially designed processing devices such as an application-specific integrated circuit (ASIC) device.

Control processor 1006 is electrically coupled to power switch 1008 and amplitude adjustment switches 1010. Power switch 1008 provides signals to control processor 1006 that cause control processor 1006 to alternate controller 102 between ON and OFF states accordingly. Amplitude adjustment switches 1010 instruct control processor 1006 to adjust the intensity of the electrical signals generated by controller 102. Electrical signals generated by control processor 1006 are passed to output stage 1016.

Output stage 1016 converts the electrical signals received from control processor 1006 to an appropriate form and then provides the electrical signals to output 1018. In this example, output stage 1016 includes MOSFET 1042 and transformer 1044. Other embodiments do not include transformer 1044, but rather use a flyback converter or other converter to generate an appropriate output signal.

Figure 22:
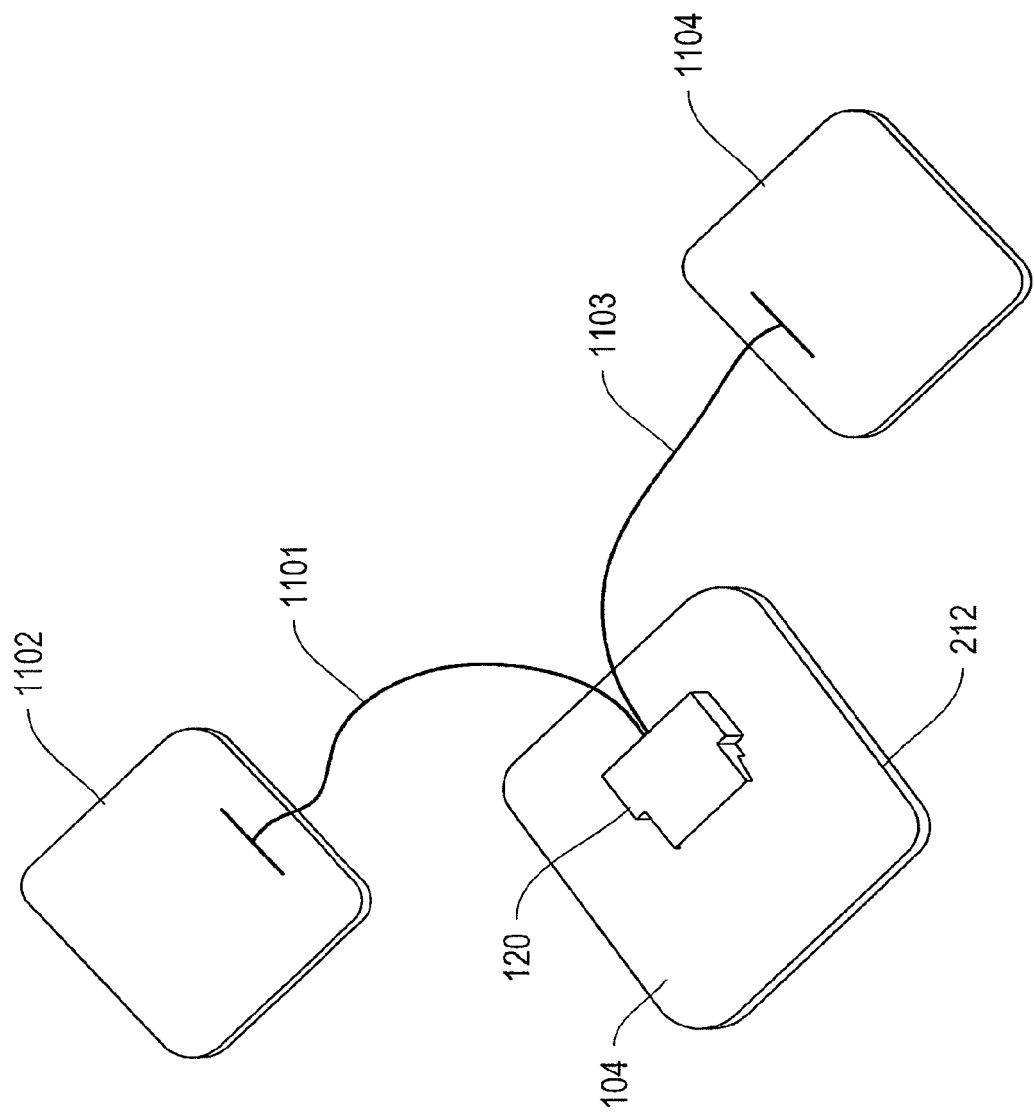
FIG. 22 is a top perspective view of another embodiment of a patch.

FIG. 22 is a top perspective view of another exemplary embodiment of patch 104. Patch 104 includes insulating layer 212 and shoe 120. Shoe 120 is connected to a surface of insulating layer 212. In this embodiment, shoe 120 includes wires 1101 and 1103 that are electrically coupled to conductors within shoe 120. Wires 1101 and 1103 are also connected at an opposite end to patches 1102 and 1104.

In one embodiment, patch 104 includes one or more electrodes, such as shown in FIG. 13, and an adhesive layer that allows patch 104 to be connected to a patient or other device. In another embodiment, patch 104 does not include an electrode, but rather passes electrical signals through wires 1101 and 1103 to patches 1102 and 1104. Patches 1102 and 1104 include one or more electrodes and can be adhered to the patient such as with an adhesive layer. The electrodes of patches 1102 and 1104 direct the electrical signals to desired therapeutic locations of the patient.

Other embodiments include any number of wires 1101 and 1103 and any number of patches 1102 and 1104 (e.g., one patch, two patches, three patches, four patches, five patches, etc.) as desired for a particular therapy. Shoe 120 includes an appropriate number of electrical conductors that can provide multiple electrical conduction channels for communicating electrical signals between controller 102 (such as shown in FIG. 12) and the patches. In some embodiments, wires 1101 and 1103 are formed adjacent to or within insulating layers to provide additional protection to the wires from damage. In some embodiments, wires 1101 and 1103 are other types of electrical conductors.

In other examples, multiple electrode sites can be positioned in a patch 104. For example, a quad-patch can be formed with an insulating layer have four lobes, with each lob having an electrode for delivery of therapy. Other configurations are possible.

Figure 23:
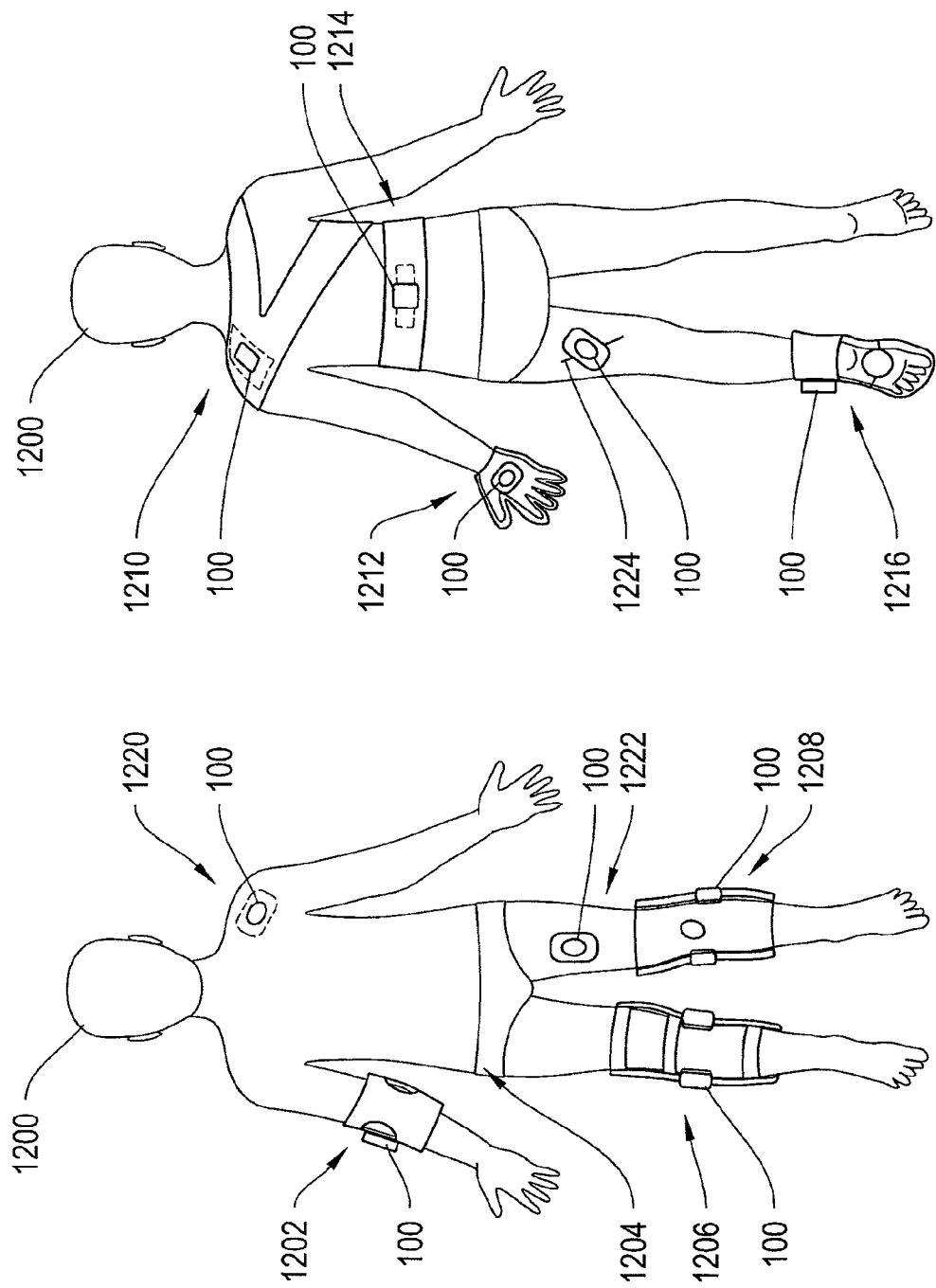
FIG. 23 is a schematic illustration of possible applications and configurations for the device shown in FIG. 12.

In some embodiments, patches 104, 1102, and 1104 do not include an adhesive layer, but rather are held in place by a band, strap, brace, built, garment, active wear, or other suitable supporting object. For example, patches can be formed integral with a supporting object or inserted within a pocket or recess of a supporting object. Some embodiments include integrated hot or cold packs. Some further examples are illustrated in FIG. 23.

FIG. 12 schematically illustrates some of the possible applications and configurations of therapeutic electrical stimulation device 100. FIG. 23 illustrates a patient 1200 including a front profile (left) and a rear profile (right).

One application of device 100 is to reduce joint pain or to reduce swelling in a joint. For example, device 100 is integrated into elbow brace 1202, hip support 1204, knee braces 1206 and 1208, shoulder brace 1210, glove 1212, back support 1214, and sock 1216 to provide relief from pain or swelling at the respective location. This illustrates that device 100 can be used to treat symptoms at the patient's elbow, hip, knee, shoulder, wrist, hand, fingers, back, ankle, foot, or any other joint in the body.

Alternatively, embodiments of device 100 are directly adhered to the desired therapeutic location, such as shoulder 1220, as described herein.

Another application of device 100 is to reduce muscle or other tissue pain at any desired therapeutic location on the body. For example, device 100 is adhered to thigh 1222 of patient 1200.

Another application of device 100 is to stimulate wound healing. For example, device 100 can be placed on or adjacent to wound 1224 (shown on the rear left thigh of patient 1200). Some embodiments of device 100 act as electronic adhesive bandage to promote wound healing and reduce pain associated with wound 1224. Some embodiments of device 100 include controller 102 and patch 104 (such as shown in FIG. 12) as a single non-separable unit.

Furthermore, alternate patch configurations (such as shown in FIG. 22) can be used to supply therapeutic electrical signals to multiple locations of the body (e.g., a back and hip) or to multiple regions of the same body part (e.g., opposite sides of the knee or top and bottom of the foot).

In some embodiments, multiple devices 100 are in data communication with each other to synchronize therapies provided by each respective device. For example, wireless communication devices (e.g., 912 shown in FIG. 20) are used to communicate between two or more devices 100.

In some embodiments, device 100 is configured to provide interferential therapy, such as to treat pain originating within tissues deeper within the body than a typical TENS device.

Some embodiments of device 100 are configured for drug delivery. Such embodiments typically include a drug reservoir (such as absorbent pads) within patch 104 (e.g., shown in FIG. 13). Iontophoresis is then used to propel the drug (such as medication or bioactive-agents) transdermally by repulsive electromotive forces generated by controller 102. An example of a suitable device for iontophoresis is described in U.S. Pat. No. 6,167,302 by Philippe Millot, titled DEVICE FOR TRANSCUTANEOUS ADMINISTRATION OF MEDICATIONS USING IONTOPHORESIS, the disclosure of which is hereby incorporated by reference in its entirety.

Other therapies can also be delivered. For example, controller 100 can be programmed to deliver microcurrent. Such microcurrent can be a constant voltage that is delivered for wound healing purposes. Other therapies can be delivered to address pain, edema, drop-foot, and other abnormalities.

Figure 24:
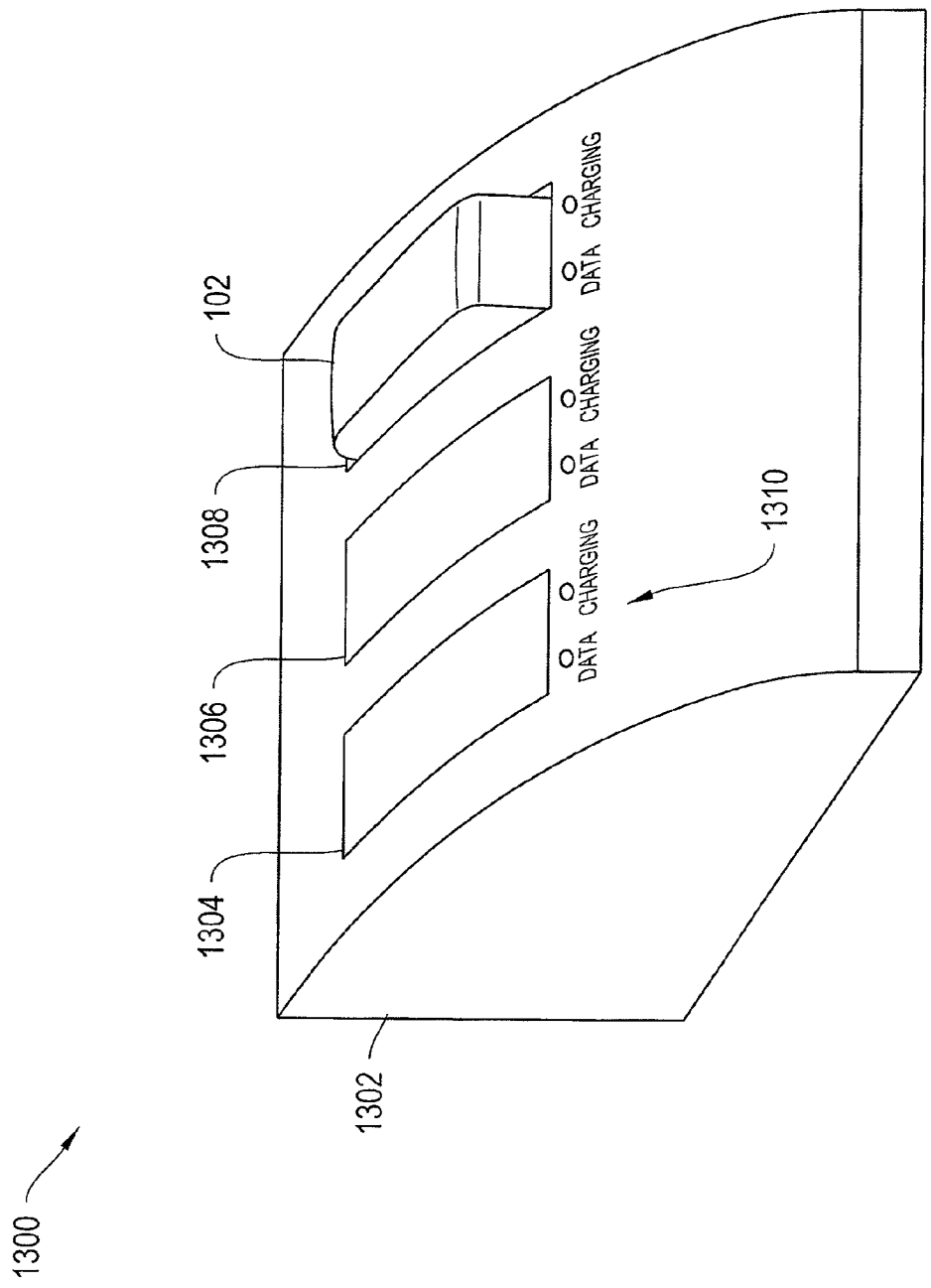
FIG. 24 is a perspective view of an exemplary docking station.

FIG. 24 is a perspective view of an exemplary docking station 1300. Docking station 1300 includes housing 1302 including multiple slots 1304, 1306, and 1308 and status indicators 1310 associated with each slot.

Each slot of the docking station 1300 is arranged and configured to receive a controller 102 of a therapeutic electrical stimulation device 100, such that multiple controllers 102 can be connected with docking station 1300 at any time. However, some embodiments of docking station 1300 include only a single slot 1304 or other port for connection to a single controller 102. Other embodiments include any number of slots as desired.

Figure 3:
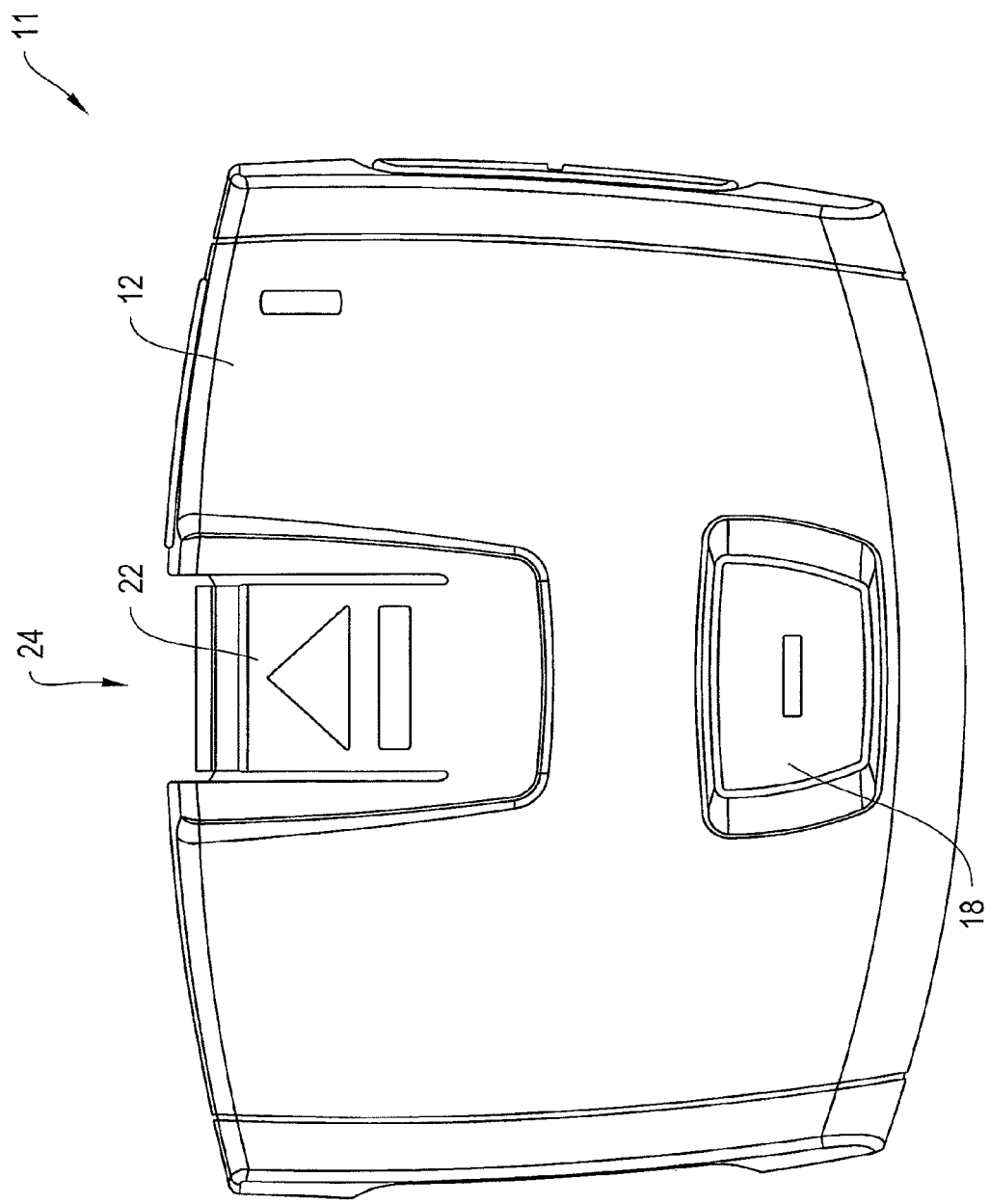
FIG. 3 is a top plan view of the controller of the therapeutic electrical stimulation device shown in FIG. 1.
Figure 4:
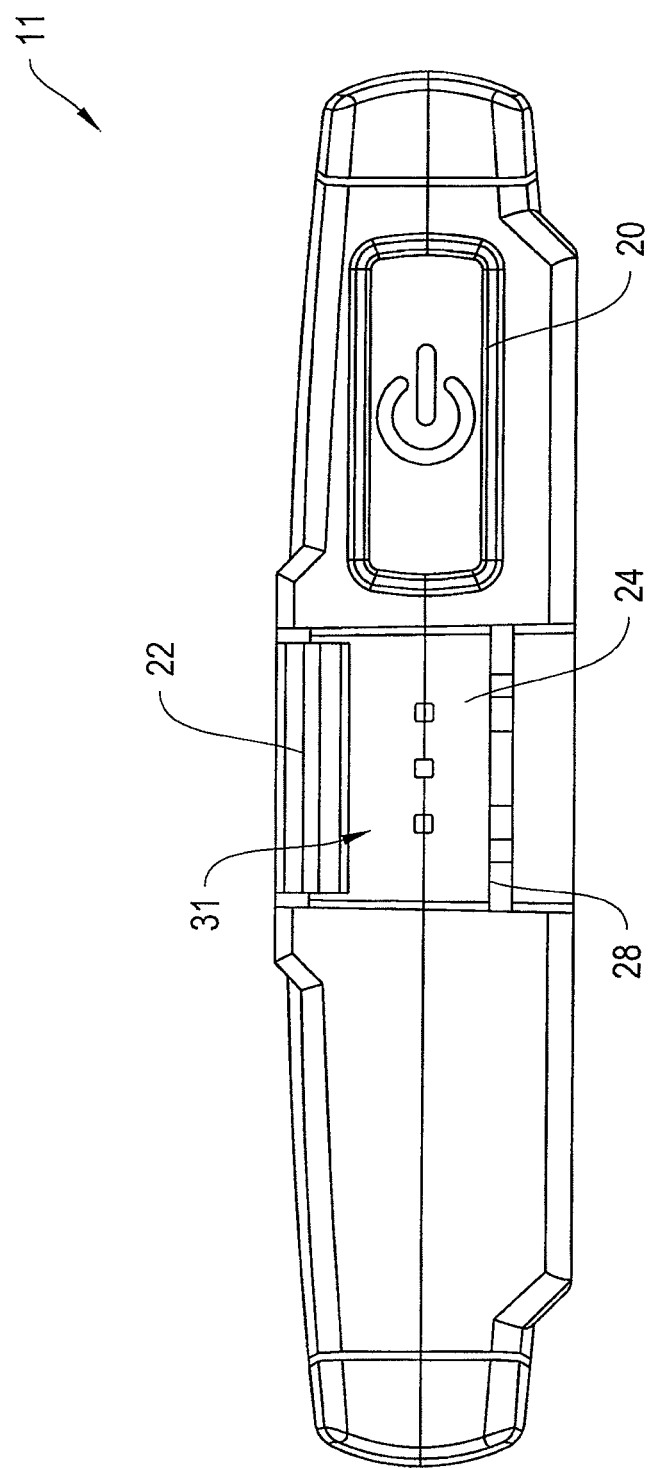
FIG. 4 is a front view of the controller of the therapeutic electrical stimulation device shown in FIG. 1.
Figure 5:
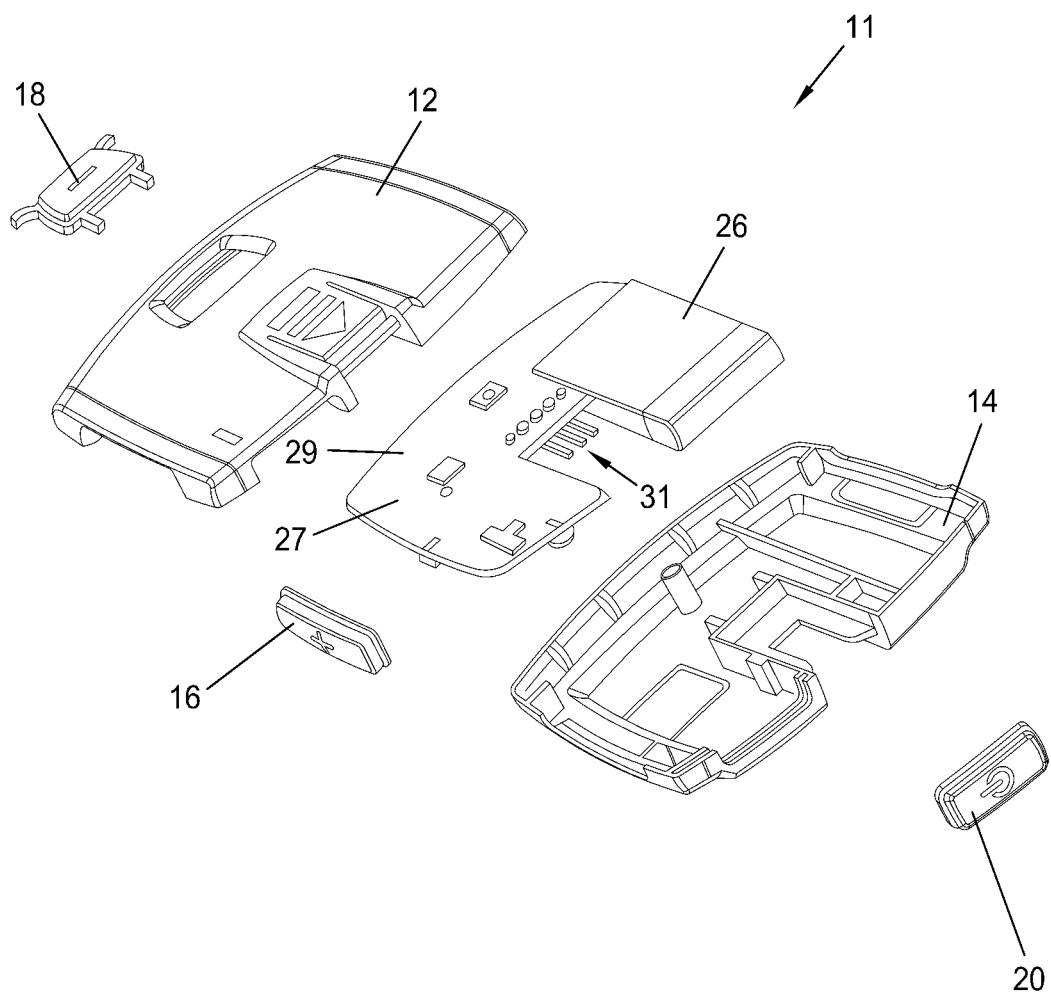
FIG. 5 is an exploded perspective view of the controller of the therapeutic electrical stimulation device shown in FIG. 1.

Docking station 1300 includes an electrical connector similar to shoe 120, such as shown in FIGS. 3-5. When device 100 is inserted into docking station 1300, shoe 120 engages with receptacle 211, such as shown in FIGS. 14-16. In this way, docking station 1300 is electrically coupled to controller 102.

In this example, docking station 1300 performs two primary functions. The first function of docking station 1300 is to recharge the battery of controller 102. To do so, docking station 1300 is typically electrically coupled to a power source such as an electrical wall outlet. Docking station 1300 converts the power from the electrical wall outlet to an appropriate form and then provides the power to the power supply (e.g., 902 shown in FIG. 20) of controller 102.

The second function of docking station 1300 is to communicate data between controller 102 and a communication network. Controller 102 can send to docking station 1300 and can receive data from docking station 1300. This function is described in more detail with reference to FIG. 25.

Some embodiments of docking station 1300 provide only one of these functions. Other embodiments provide additional features and functionality. For example, some embodiments of docking station 1300 allow multiple devices 100 to communicate with each other when connected with docking station 1300. In other examples, docking station 1300 is also configured to communicate with one or more computers accessible through a network, as described below.

Docking station 1300 includes status indicators 1310 associated with each slot of docking station 1300. In this example, status indicators 1310 include a data communication indicator and a charging indicator. The data communication indicator is a light emitting diode (LED) that illuminates when the docking station 1300 is communicating with the respective controller 102. The charging indicator is an LED that illuminates when docking station 1300 is charging the respective controller 102. Other embodiments include additional status indicators 1310. Other types of status indicators include audible status indicators (e.g., speakers, buzzers, alarms, and the like) and visible status indicators (e.g., lights, liquid crystal displays, display screens, and the like).

Docking station 1300 is not limited to connection with a single type of controller 102. Multiple types of controllers 102 can be connected with docking station 1300 at any one time, if desired. For example, controllers 102 include a TENS device, an iontophoresis device, a muscle stimulation device (e.g., a neuromuscular electrical stimulation (NMES) device), a wound healing device, an interferential device, or other devices.

In some examples, docking station 1300 is configured to be used at a patient's home, such as in a bathroom or kitchen. Docking station 1300 can include multiple stations for charging different types of devices, as well as drawers and other conveniences that allow docking station 1300 to be used for multiple purposes.

Figure 25:
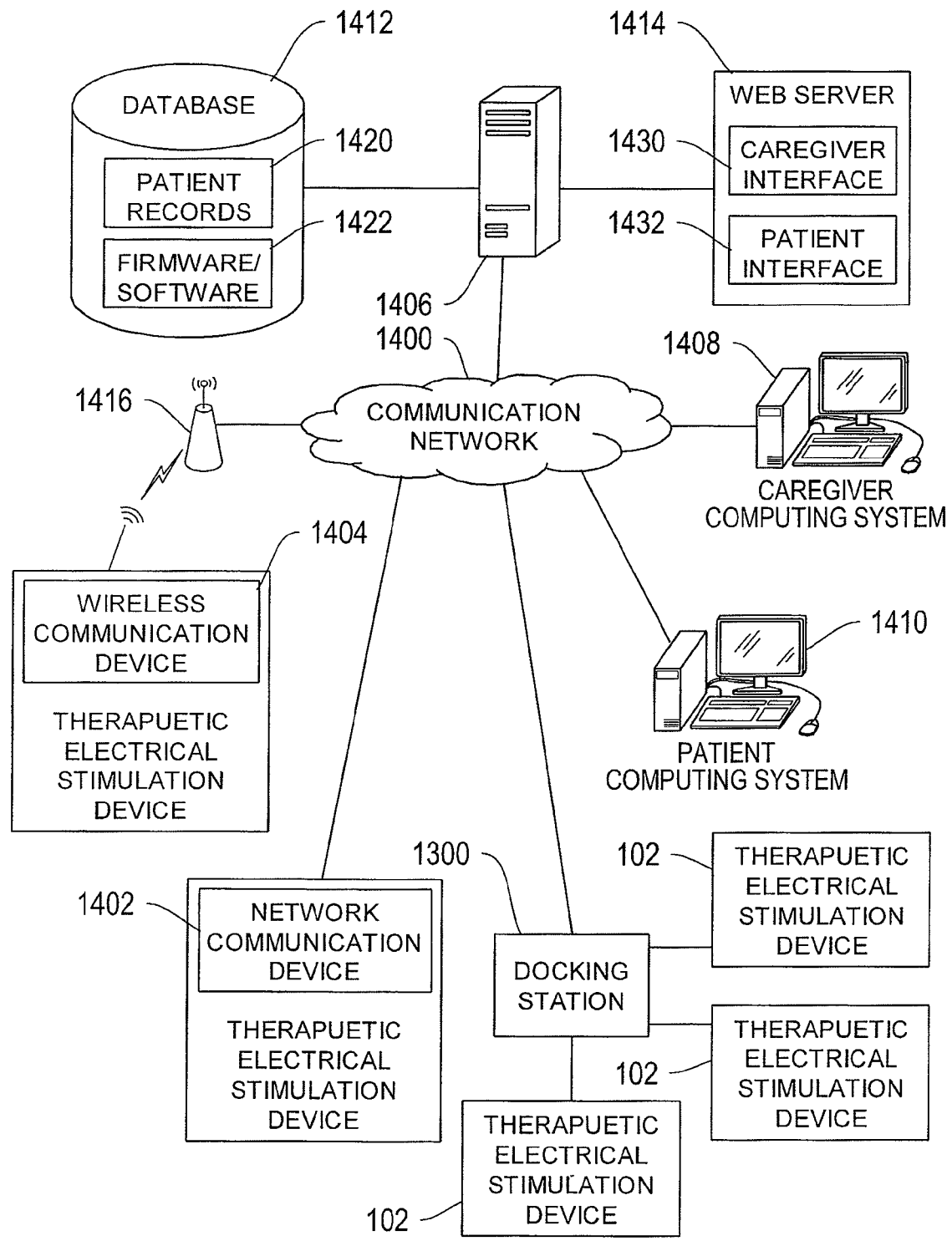
FIG. 25 is a block diagram of an exemplary system for communicating across a communication network including the device shown in FIG. 12.

FIG. 25 is a block diagram of an exemplary system for communicating across communication network 1400 involving therapeutic electrical stimulation devices. The system includes devices 102, 1402, and 1404. Devices 102 are in data communication with docking station 1300, such as shown in FIG. 24. Device 1402 includes a wireless communication device and device 1404 includes a wired network communication device. The system also includes server 1406, caregiver computing system 1408, and patient computing system 1410. Server 1406 includes database 1412 and Web server 1414. System also includes wireless router 1416.

Communication network 1400 is a data communication network that communicates data signals between devices. In this example, communication network 1400 is in data communication with docking station 1300, device 1402, device 1404, server 1406, caregiver computing system 1408, patient computing system 1410, and wireless router 1416. Docking station 1300 is in data communication with devices 102. Wireless router 1416 is in data communication with device 1404. Examples of communication network 1400 include the Internet, a local area network, an intranet, and other communication networks.

In some embodiments, devices 102, 1402, and 1404 store, in memory, data relating to therapy delivery or other operational characteristics of the respective devices. Communication network 1400 can be used to communicate that data to another device. For example, the data is transferred to patient computing system 1410 or to caregiver computing system 1408. Once the data has been transferred to the computing system, the data is stored for review and analysis by the patient or the caregiver. Communication network 1400 can also be used to communicate data from devices 102, 1402, and 1404 to server 1406. Server 1406 stores the data in patient record 1420.

In some embodiments, server 1406 includes Web server 1414. Web server 1414 includes caregiver interface 1430 patient interface 1432. Additional interfaces are provided in some embodiments to third parties, such as an insurance company. Web server 1414 generates web pages that are communicated across communication network 1400 using a standard communication protocol. An example of such a protocol is hypertext transfer protocol. The webpage data is arranged in a standard form, such as hypertext markup language. The webpage data is transferred across communication network 1400 and received by computing system 1408 and computing system 1410. A browser operating on respective computing system reads the webpage data and displays the webpage to the user.

Caregiver interface 1430 generates a webpage intended for use by a caregiver. The caregiver interface 1430 allows the caregiver to access patient records 1420 and generates reports or graphs to assist the caregiver in analyzing data from patient records 1420. In addition, caregiver interface 1430 provides technical or medical suggestions to the caregiver. In some embodiments, caregiver interface 1430 also allows the caregiver to request adjustments to an operational mode of a device 102, 1402, or 1404. The operational mode adjustments are then communicated from server 1406 to the device, and the device makes the appropriate mode adjustments.

Patient interface 1432 generates a webpage intended for use by a patient. In one example, patient interface 1432 allows the patient to access patient records 1420 and generates reports or graphs that assist the patient in analyzing data from patient records 1420. Patient interface 1432 provides instructions to assist the patient with uploading data from device 102, 1402, or 1404 to patient records 1420. Instructions or other educational information is also provided by patient interface 1432, if desired.

In some embodiments, database 1412 includes firmware repository 1422. Firmware repository 1422 includes data instructions that define the logical operation of a controller 102 (e.g. firmware 934 shown in FIG. 20). Firmware repository 1422 is used in some embodiments to store various versions of firmware. For example, when a new firmware version is created, the developer stores the new version of firmware in the firmware repository 1422. The firmware is then communicated to the appropriate devices 102, 1402, or 1404. The communication of new firmware versions can be either automatically distributed, or provided as an option to a patient or caregiver through interfaces 1430 and 1432. In some embodiments, patient interface 1432 requires that a patient agree to pay for an upgraded firmware version before the firmware is made available for installation on a device.

In another embodiment, firmware repository 1422 includes different firmware algorithms. Each firmware algorithm is specifically tailored to provide a specific therapy when executed by devices 102, 1402, 1404 or to be used with a particular hardware configuration. Examples of therapies defined by separate firmware algorithms include TENS, interferential therapy, edema therapy, muscle stimulation, iontophoresis therapy, and other therapies. A different firmware algorithm can also be specifically tailored for particular hardware configurations, such as for particular electrode numbers or configurations, for particular data communication devices, for different docking stations, or to accommodate other differences in hardware configuration.

For example, a patient may first obtain a TENS device including a patch shown in FIG. 12. The device includes a first firmware type that defines an algorithm appropriate for TENS therapy. Later, the patient desires to upgrade the device to cause the device to operate as an iontophoresis device. To do so, the patient uses patient computing system 1410 to access patient interface 1432. The patient selects a new firmware algorithm that is designed for iontophoresis therapy. The patient purchases and downloads the firmware associated with the iontophoresis therapy and loads the firmware onto the device. If necessary, an appropriate patch can be purchased through patient interface 1432 and delivered to the patient. The patch is then connected to the device controller and the new firmware algorithm is executed. The firmware causes the device to provide the desired iontophoresis therapy. In this way, some embodiments of controller 102 are customizable to provide multiple different therapies.

In another embodiment, firmware is specially tailored for providing a therapy to a particular part of the body. As a result, separate firmware algorithms are available for the treatment of separate body parts and conditions associated with those body parts. Such firmware algorithms can be obtained by downloaded, as described above.

In some embodiments, controllers 11, 100 include graphical user interfaces that allow the user to control the controllers 11, 100 and the therapy provided thereby. For example, the controllers can include built-in displays that are used to present the user interfaces. The user interfaces have home pages that allow the user to control various aspects of the controller, such as turning the device on and off, the type of therapy provided, and the intensity of the therapy.

In other examples, a separate device is used to control the controllers 11, 100. This device can communicate with the controllers 11, 100 through wired or wireless means (e.g., Wifi, Bluetooth). For example, a docking station (e.g., docking station 1300 described above) can include a user interface that is programmed to control the therapy provided by controllers 11, 100. The docking station can communicate wirelessly with controllers 11, 100.

In some examples, controllers 11, 100 can include additional functionality, such as open lead detection. If a lead looses contact with a surface that is being delivered therapy, controllers 11, 100 are programmed to detect the open lead and to modify therapy appropriately until the lead again makes contact. For example, controllers 11, 100 can be programmed to shut down therapy that is delivered to the open lead and to issue an alarm so that the user can replace the lead.

In other examples, controllers 11, 100 are programmed to sense feedback from the user and modify therapy accordingly. For example, controllers 11, 100 can be programmed to sense electromyographic biofeedback based on muscle activity and regulate therapy accordingly. In other examples, controllers 11, 100 are programmed to sense impedance and deliver therapy accordingly. In other examples, other biofeedback such as heart rate or activity levels can also be monitored. Other configurations are possible.

In some examples, the user can provide specific feedback as well. For example, the user can set pain thresholds that controllers 11, 100 are programmed to remember. In other examples, the pain thresholds can be set automatically by controllers 11, 100 by monitoring capacitance levels.

In yet other examples, controllers 11, 100 can include accelerometers and/or gyroscopes that can be used to measure orientation and activity level of the patient. For example, therapy can be adjusted based on the orientation of the patient (e.g., lying down or upright), as well as activity level. Controllers 11, 100 can be programmed to adjust therapy over a specific time. In yet other examples, multiple controllers can be used, and the controllers can be programmed to communicate with each other to synchronize the therapy that is delivered to the user, thereby forming a body area network. This network can be formed through wireless communication and/or conductive communication through the patient's body.

The number of delivery channels can be modified (e.g., 2 channel vs. 4 channel) to modify the type and intensity of therapy. Also, devices can be connected in series to deliver an increase in therapy intensity or increase the area treated.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A system for delivering therapeutic electrical stimulation, the system including a controller comprising:
    a power source;
    an electrical signal generator powered by the power source and configured to generate an electrical signal; and
    a receptacle comprising at least one conductor, wherein the conductor is configured to couple to the electrical signal generator to receive the electrical signal, wherein the receptacle is configured to receive a portion of a patch so as to electrically couple a portion of the patch to the conductor, wherein the receptacle comprises a detent configured to capture the portion of the patch to retain the portion of the patch within the receptacle.

2. The system of claim 1, further comprising:
    the patch for a therapeutic electrical stimulation device, the patch comprising an insulating layer having a first side and a second side, the patch further comprising at least two electrodes adjacent the second side of the patch; and
    a shoe configured for configured for insertion into the receptacle and connection to the first side of the patch, the shoe comprising at least two conductors, wherein each conductor configured for electrical coupling to one of the electrodes.

3. The system of claim 2, wherein the shoe comprises a first portion that is normal to the first side of the insulating layer and a second portion that is angled from the first portion.

4. The system of claim 3, wherein the second portion is angled about ninety degrees from the first portion.

5. The system of claim 4, wherein the shoe includes a member that is partially captured by the detent defined by a controller in the receptacle to retain the shoe within the receptacle.

6. The system of claim 5, wherein the controller operates to generate electrical signals for at least one action selected from the group consisting of transcutaneous electrical nerve stimulation, drug delivery, iontophoresis therapy, edema reduction, wound healing, and interferential current therapy.

* * * * *

UNITED STATES PATENT AND TRADEMARK OFFICE
CERTIFICATE OF CORRECTION

| | | Page 1 of 1 |
|---|---|---|
| PATENT NO. | : 8,977,366 B2 | |
| APPLICATION NO. | : 14/322838 | |
| DATED | : March 10, 2015 | |
| INVENTOR(S) | : Thomas Jerome Bachinski et al. | |

It is certified that error appears in the above-identified patent and that said Letters Patent is hereby corrected as shown below:

In the Drawings

Sheet 30 of 30 (Reference Numeral 1404, FIG. 25) at line 4, Change "THERAPUETIC" to --THERAPEUTIC--.

Sheet 30 of 30 (Below Reference Numeral 1410, FIG. 25) at line 3 (approx.), Change "THERAPUETIC" to --THERAPEUTIC--.

Sheet 30 of 30 (Reference Numeral 1402, FIG. 25) at line 4, Change "THERAPUETIC" to --THERAPEUTIC--.

Sheet 30 of 30 (Below Reference Numeral 1410, FIG. 25) at line 7 (approx.), Change "THERAPUETIC" to --THERAPEUTIC--.

Sheet 30 of 30 (Below Reference Numeral 1300, FIG. 25) at line 4 (approx.), Change "THERAPUETIC" to --THERAPEUTIC--.

In the Specification

In column 2 at line 63, Change "1" to --1.--.

In column 2 at line 65, Change "1" to --1.--.

In column 4 at line 34, Change "show" to --portion--.

In column 4 at line 50, After "the" insert --portion--.

In column 5 at line 12, Change "show" to --portion--.

In column 14 at line 41, Change "Amtel" to --Atmel--.

In the Claims

In column 20 at line 39, In Claim 2, after "shoe" delete "configured for".

Signed and Sealed this
Twenty-ninth Day of December, 2015

Michelle K. Lee
*Director of the United States Patent and Trademark Office*